US010806539B1

(12) United States Patent
Richter et al.

(10) Patent No.: US 10,806,539 B1
(45) Date of Patent: Oct. 20, 2020

(54) ADJUSTABLE PATIENT REFERENCE ARRAY

(71) Applicant: Medos International Sarl, Le Locle (CH)

(72) Inventors: Joern Richter, Kandern (DE); Laura Naikauskiene, Rotkreutz (CH)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 16/412,635

(22) Filed: May 15, 2019

(51) Int. Cl.
*A61B 90/57* (2016.01)
*A61B 34/20* (2016.01)
*A61B 90/00* (2016.01)

(52) U.S. Cl.
CPC .............. *A61B 90/57* (2016.02); *A61B 34/20* (2016.02); *A61B 2034/2072* (2016.02); *A61B 2090/3983* (2016.02)

(58) Field of Classification Search
CPC . A61B 90/57; A61B 34/20; A61B 2034/2072; A61B 2090/3983
See application file for complete search history.

(56) References Cited

U.S. PATENT DOCUMENTS

| | | | |
|---|---|---|---|
| 6,856,828 B2 | 2/2005 | Cossette et al. | |
| 7,753,910 B2 | 7/2010 | Ritland | |
| 7,780,681 B2 | 8/2010 | Sarin et al. | |
| 8,317,844 B2 | 11/2012 | Maier et al. | |
| 8,706,185 B2 | 4/2014 | Foley et al. | |
| 9,005,211 B2 | 4/2015 | Brundobler et al. | |
| RE45,509 E | 5/2015 | Foley et al. | |
| 9,585,700 B2 | 3/2017 | Wehrle et al. | |
| 2008/0154262 A1 | 6/2008 | Brundobler et al. | |
| 2012/0232377 A1 | 9/2012 | Nottmeier | |
| 2015/0257851 A1 | 9/2015 | Plassky et al. | |

(Continued)

FOREIGN PATENT DOCUMENTS

WO 2017/221257 A1 12/2017

OTHER PUBLICATIONS

Brainlab, Cleaning, Disinfection and Sterilization Guide, Revision 5.2, 2016, 180 pages.

(Continued)

*Primary Examiner* — Anita M King
(74) *Attorney, Agent, or Firm* — BakerHostetler

(57) ABSTRACT

In one embodiment, an impact absorber attaches a reference array of a computer-assisted surgery system to a medical implant. The impact absorber has a coupler that couples the reference array to the implant such that the reference array is rotatable relative to the implant from an undeflected orientation to a deflected orientation when an external impacting force is applied to the reference array, and from the deflected orientation to the undeflected orientation when the external force is removed. The impact absorber has an alignment feature that 1) engages with a corresponding alignment feature so as to align the reference array with the undeflected orientation and 2) disengages from the corresponding alignment feature when the reference array is rotated from the undeflected orientation to the deflected orientation. Allowing the reference array to be returned to the undeflected orientation after it is impacted can avoid a need to recalibrate the system.

20 Claims, 9 Drawing Sheets

(56) References Cited

U.S. PATENT DOCUMENTS

| | | |
|---|---|---|
| 2017/0135733 A1* | 5/2017 | Donner .............. A61B 17/7058 |
| 2017/0360515 A1 | 12/2017 | Kozak et al. |
| 2018/0092699 A1 | 4/2018 | Finley |
| 2018/0199951 A1 | 7/2018 | Chappuis et al. |
| 2018/0206860 A1 | 7/2018 | Van et al. |
| 2018/0214016 A1 | 8/2018 | Thommen et al. |
| 2018/0289426 A1 | 10/2018 | Dace |
| 2019/0231446 A1* | 8/2019 | Bowling ................ A61B 34/30 |

OTHER PUBLICATIONS

Brainlab, HIP, Instrument User Guide, Revision 1.1, 2015, 110 pages.

DePuy Synthes, Navigation-Ready Instrument Catalog, Feb. 2016, 20 pages.

Mezger et al., Navigation in surgery, Langenbeck's Archives of Surgery, Apr. 1, 2013;398(4):501-514.

* cited by examiner

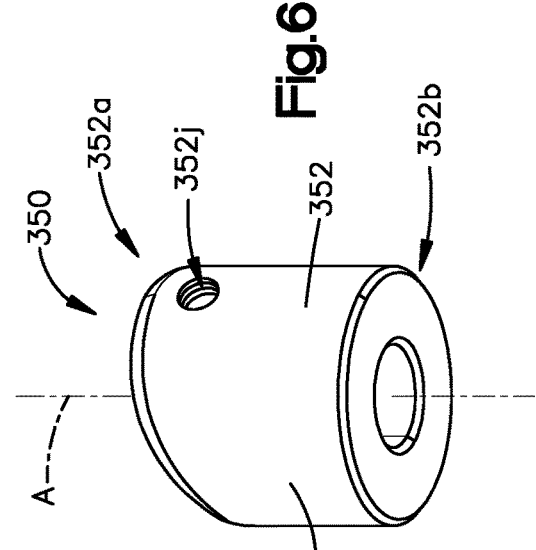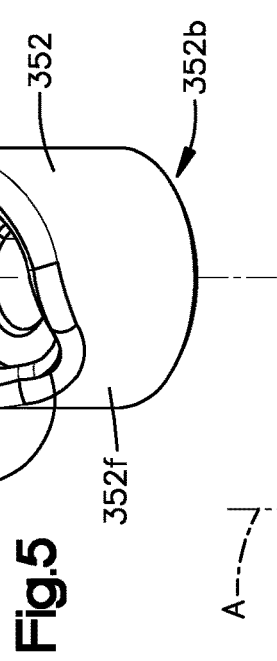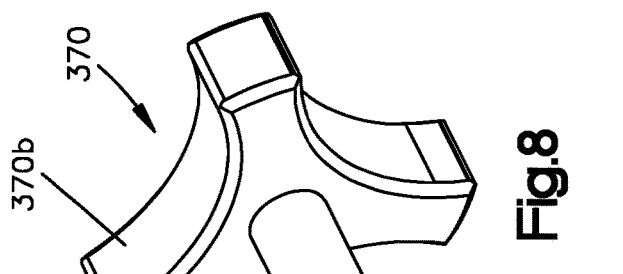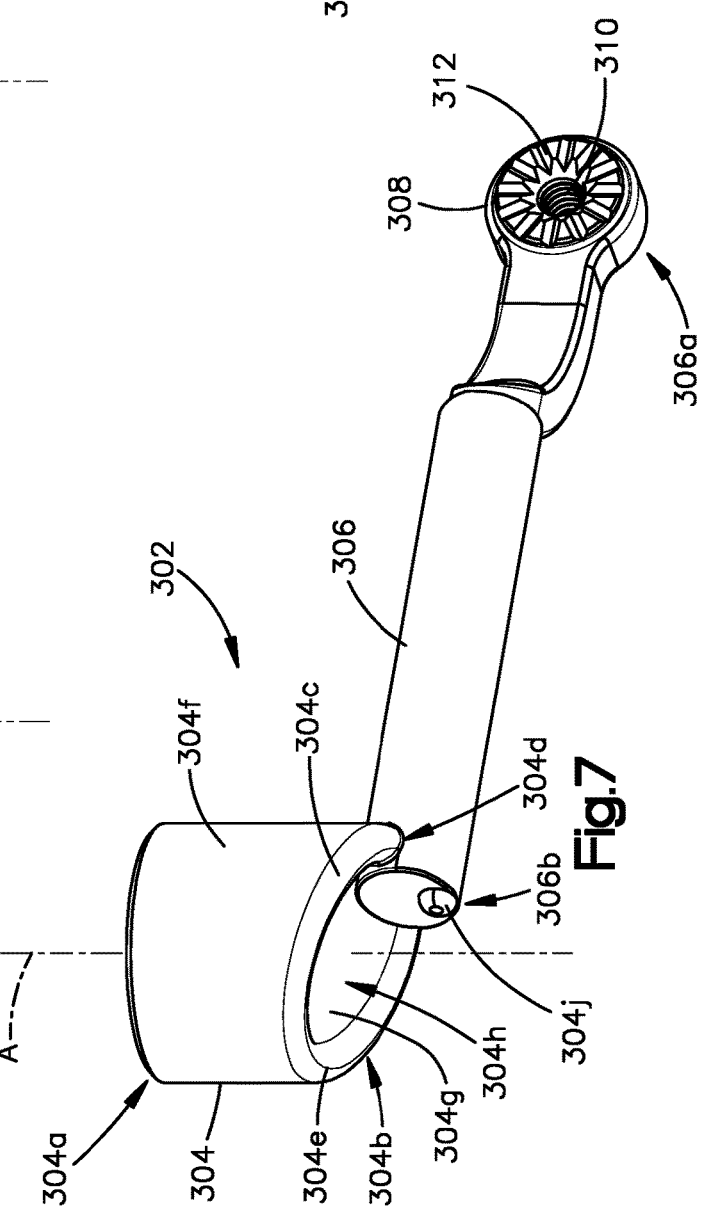

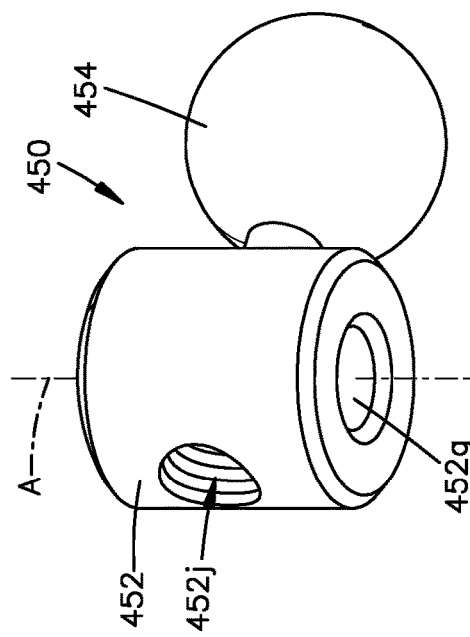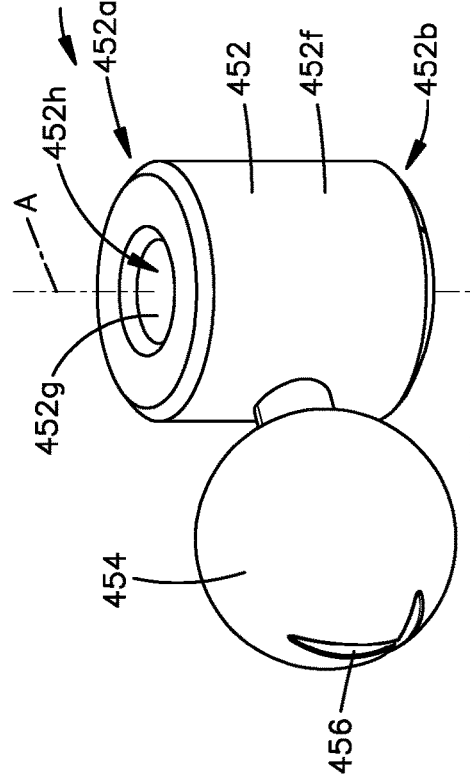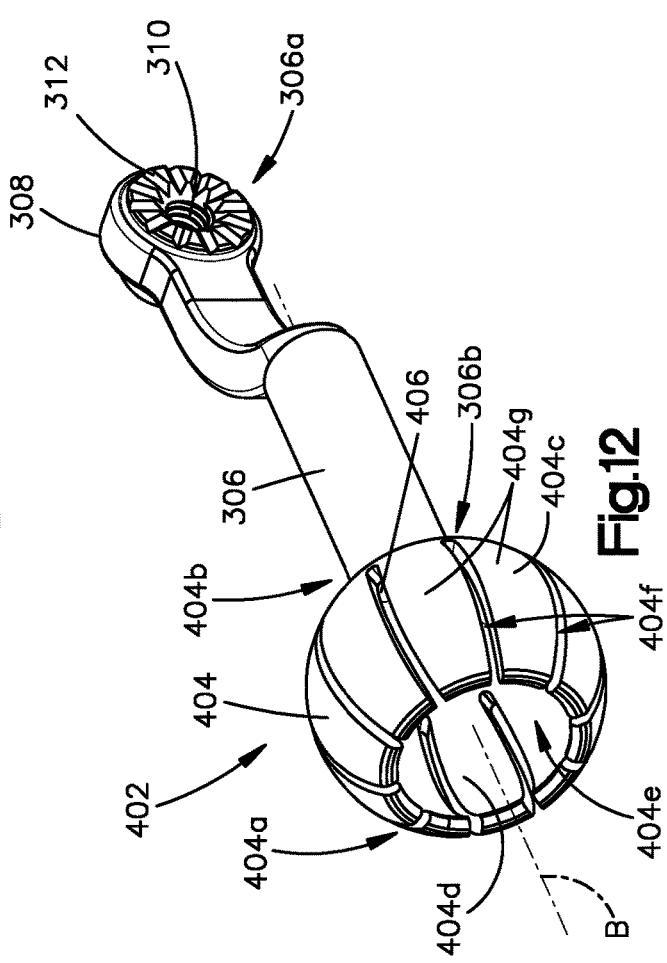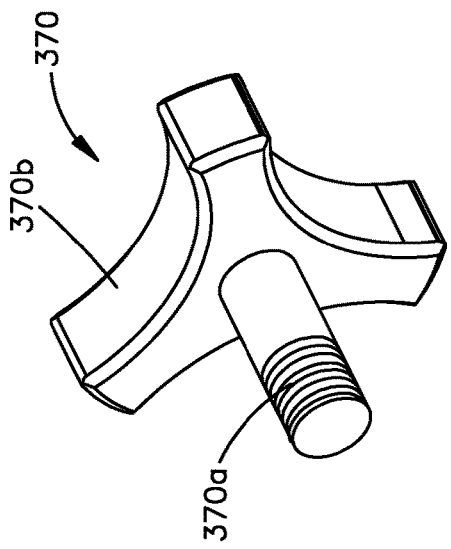

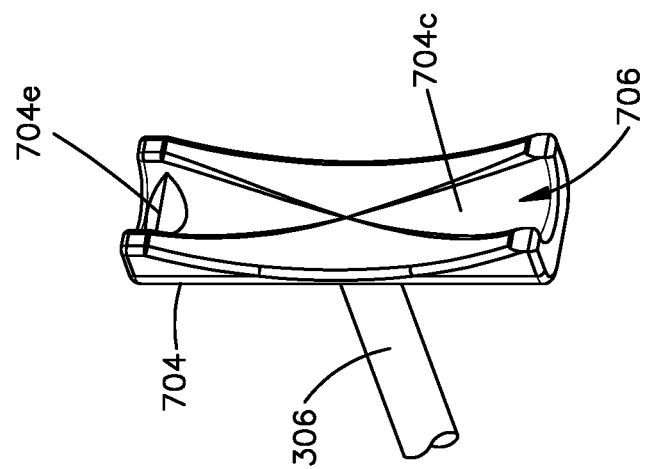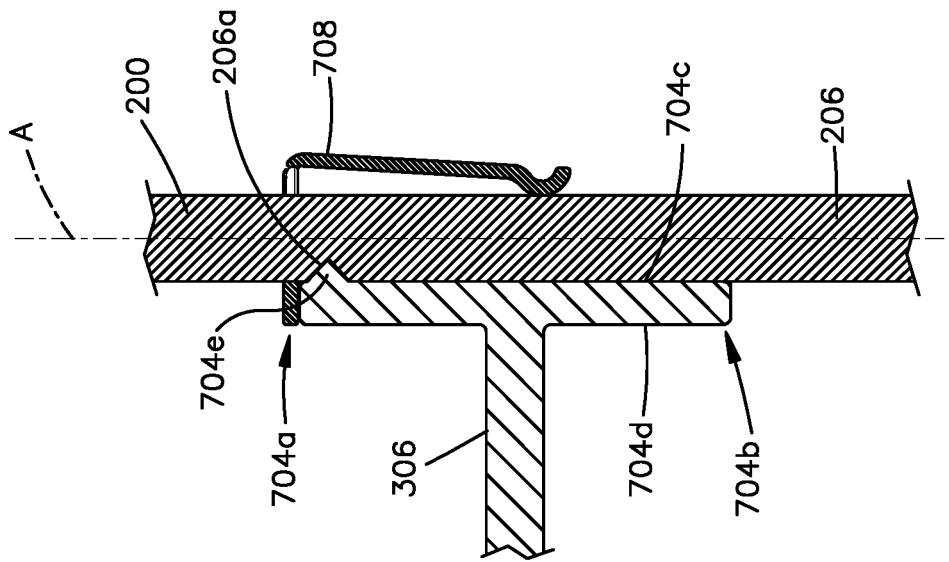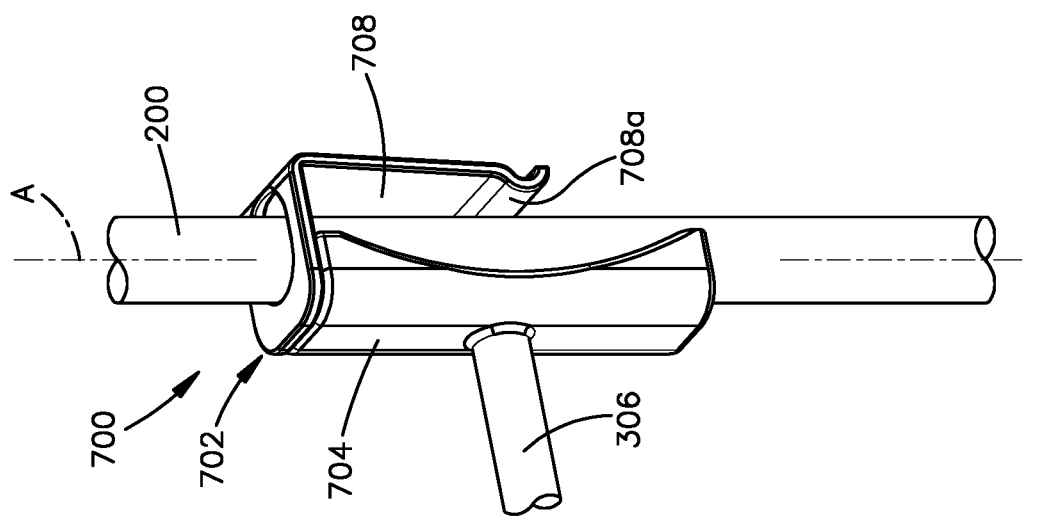

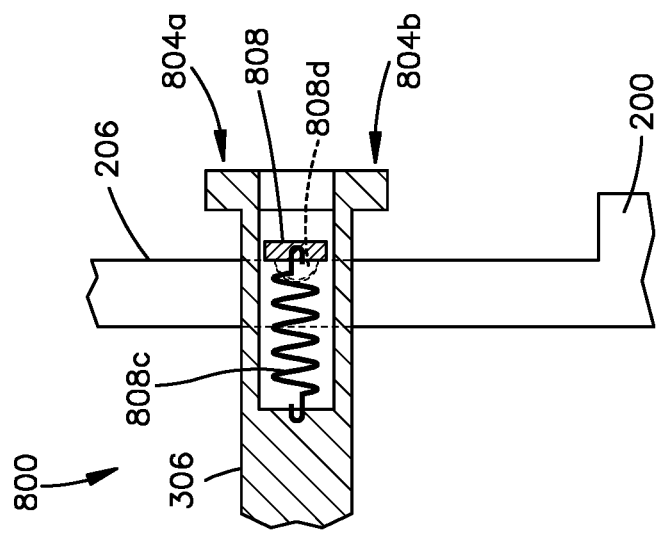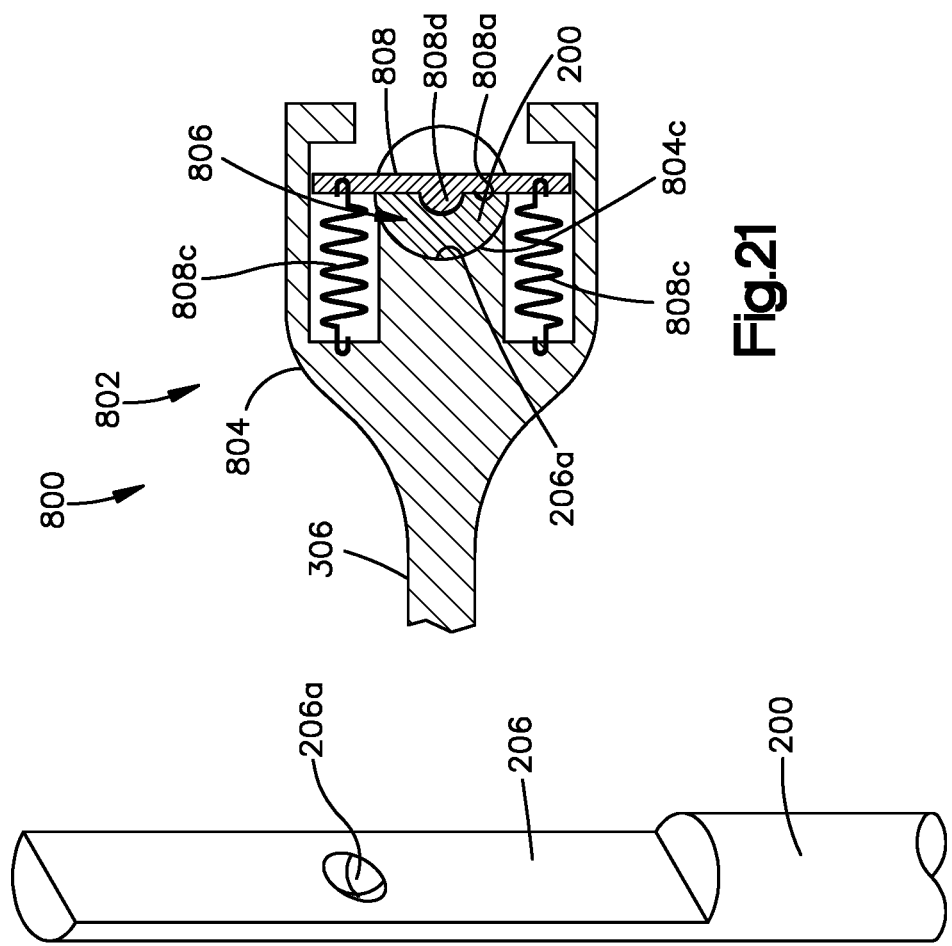

ADJUSTABLE PATIENT REFERENCE ARRAY

BACKGROUND

Computer-assisted surgery employs computer technology for surgical planning and for guiding surgical instruments during a surgery. Typically, in performing a computer-assisted surgery, a three-dimensional model of the patient is generated using medical imaging technologies such as one or more of MRI, CT scan, x-rays, and ultrasound. Sensors are positioned over the patient, and a computer system tracks movement of the surgical instruments relative to the three-dimensional model of the patient as the surgical instruments are sensed by the sensors. To aid in tracking movement of the surgical instruments, a patient reference array is typically attached to the patient prior to image collection that provides at least one reference point. The computer of the computer-assisted surgery system is calibrated to the at last one reference point, and then positioning of the instruments can be tracked by the computer system relative to the at least one reference point. Surgeries performed using computer-assisted surgery techniques can typically reduce an amount of x-ray exposure to the patient compared to conventional non-computer assisted surgery techniques, and can often result in more accurate placement of medical implants.

SUMMARY

In accordance with one aspect of the present disclosure, an impact absorber comprises a body configured to support a reference array of a computer-assisted surgery system. The body comprises a coupler that is configured to couple to at least one of 1) a shaft of a medical implant and 2) a second body of the impact absorber that is configured to couple to the shaft. The reference array is rotatable with the body at least partially about the shaft from an undeflected orientation to a deflected orientation when an external force is applied to the reference array and from the deflected orientation to the undeflected orientation when the external force is removed from the reference array so as to realign the reference array in the undeflected orientation.

In accordance with another aspect, an impact absorber comprises a body defining a coupler configured to couple a reference array of a computer-assisted surgery system to at least one of 1) a medical implant and 2) a second body of the impact absorber that is configured to couple to the medical implant. The reference array is movable with the body relative to the medical implant from an undeflected orientation to a deflected orientation when an external force is applied to the reference array and from the deflected orientation to the undeflected orientation when the external force is removed from the reference array. The body defines an alignment feature that is configured to 1) disengage from a corresponding alignment feature when the reference array is moved from the undeflected orientation to the deflected orientation and 2) engage with the corresponding alignment feature when the reference array is moved from the deflected orientation to the undeflected orientation so as to realign the reference array in the undeflected orientation.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted. In the figures:

FIG. 5 shows a perspective view of a body of the impact absorber of FIG. 1 according to one embodiment, the first body defining a coupler configured to couple the reference array to the medical implant;

FIG. 6 shows another perspective view of the body of FIG. 5;

FIG. 7 shows a perspective view of another body of the impact absorber of FIG. 1 according to one embodiment, the body configured to movably couple to at least one of the body of FIGS. 5 and 6 and the medical implant;

FIG. 8 shows a perspective view of a fastener of the impact absorber of FIG. 1 according to one embodiment, the fastener configured to couple the body of FIGS. 5 and 6 to the medical implant;

FIG. 10 shows a perspective view of a body of the impact absorber of FIG. 9 according to one embodiment, the body defining a coupler being configured to couple the reference array to the medical implant;

FIG. 11 shows another perspective view of the body of FIG. 10;

FIG. 12 shows a perspective view of another body of the impact absorber of FIG. 9 according to one embodiment, the body defining a coupler configured to couple to the body of FIGS. 10 and 11; and FIG. 13 shows a perspective view of a fastener of the impact absorber FIG. 9 according to one embodiment, the fastener configured to couple the body of FIGS. 10 and 11 to the medical implant;

FIG. 17 shows an assembled perspective view of a portion of a system having an impact absorber that couples a patient reference array to a medical implant according to even yet another embodiment of the disclosure;

FIG. 18 shows a cross-sectional elevation view of the portion of the system of FIG. 17;

FIG. 19 shows a perspective view of a body of the impact absorber of FIG. 17 according to one embodiment;

FIG. 20 shows a perspective view of a portion of a medical implant according to one embodiment;

FIG. 21 shows a cross-sectional plan view of an impact absorber according to yet still another embodiment, the impact absorber being coupled to the medical implant of FIG. 20; and FIG. 22 shows a cross-sectional elevation view of the impact absorber of FIG. 21 coupled to the medical implant of FIG. 20.

DETAILED DESCRIPTION

Figure 1:
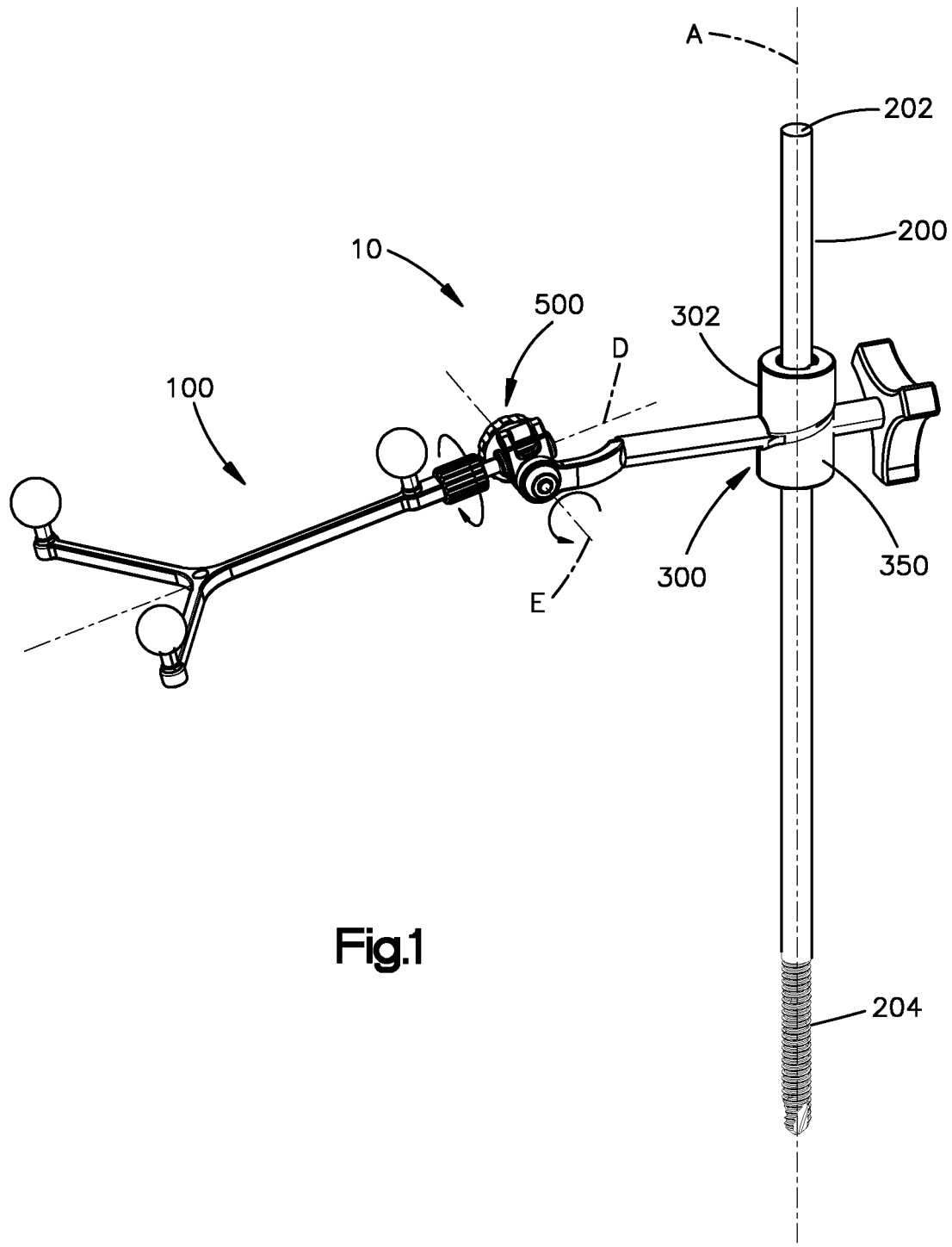
FIG. 1 shows a perspective view of a system having an impact absorber that couples a patient reference array to a medical implant according to one embodiment of the disclosure.

Typically, reference arrays are attached to a patient at, or near, the surgical location. As a result, reference arrays are often susceptible to being inadvertently impacted by a healthcare professional or surgical instrument. Therefore, conventional reference array systems are designed to be rigidly affixed the bone so as to prevent deflection of the reference array, and consequently, prevent recalibration of the system. If the external force exerted by the healthcare professional or surgical instrument is significant enough to move or deflect the reference array, then calibration of the computer-assisted surgery system can be lost, thereby requiring the system to be recalibrated. This can lead to costly time delays to recalibrate the system, or worse, can result in errors in the medical procedure if the loss of calibration is not detected. In some cases, deflection of the reference array can cause damage to the bone when the attachment to the bone moves relative to the bone. Instead of rigidly affixing the reference array to the bone, the reference array can be attached to a medical implant and configured such that the reference array is permitted to 1) deflect relative to the medical implant so as to not move the medical implant relative to the bone and 2) be subsequently realigned relative to the medical implant in the undeflected, calibrated position after deflecting, so as to avoid a need to recalibrate the computer-assisted surgery system.

Referring to the figures, according to various embodiments of the present disclosure, a system 10 is configured to attach a patient reference array 100 of a computer-assisted surgery system to a patient, such as a vertebra of the patient. In general, the system 10 comprises an impact absorber (e.g., 300, 400, 600, 700, 800) that is configured to couple the patient reference array 100 to a medical implant 200, such as a Schanz screw or pedicle screw, such that the patient reference array 100 is movable relative to the medical implant 200. The system 10 can optionally comprise at least one of the reference array 100 and the medical implant 200, although it will be understood that the reference array 100 and the medical implant 200 can be separate from the system 10. In some embodiments, the impact absorber 300 can be configured to permit the reference array 100 to rotate relative to the medical implant 200, such as at least partially about a shaft of the medical implant 200. In some embodiments, the reference array 100 can rotate about an axis that extends along the axial direction, such as about the central axis A of the medical implant 200 or about an axis that is substantially parallel to the central axis A. In some such embodiments, the rotation can be pivoting about a pivot point. Thus, in such embodiments, the reference array 100 can be pivotable relative to the medical implant 200. Although the following discussion refers to rotation, it will be understood, that movements other than rotation and pivoting of the reference array 100, such as translation, are contemplated.

The impact absorber (e.g., 300, 400, 600, 700, 800) is configured so as to permit the patient reference array 100 to move (e.g., rotate) relative to the medical implant 200 from an undeflected orientation to a deflected orientation when an external force is applied to at least one of the patient reference array 100 and the impact absorber. The rotating can be non-destructive to the impact absorber, the medical implant 200, and the reference array 100. In other words, the rotating can be performed without bending or deforming the impact absorber, the medical implant 200, or the reference array 100. The undeflected orientation can be an orientation of the patient reference array 100 to which the computer-assisted surgery system is, or will be, calibrated so as to track movements of surgical devices and instruments.

The external force can be a force applied by, for example, a person or instrument impacting the at least one of the patient reference array 100 and the impact absorber. The impact absorber (e.g., 300, 400, 600, 700, 800) can be configured such that an amount of external force needed to rotate the reference array 100 relative to the medical implant 200 is less than an amount of external force needed to cause the medical implant 200 to move relative to a bone to which the medical implant 200 is affixed. Thus, the impact absorber (e.g., 300, 400, 600, 700, 800) can be configured to move the patient reference array 100 so as to absorb the external force, thereby limiting an amount of the external force applied to the medical implant 200, and in some cases, preventing the external force from being applied to the medical implant 200 altogether.

The impact absorber (e.g., 300, 400, 600, 700, 800) is further configured permit the patient reference array 100 to move (e.g., rotate) relative to the medical implant 200 from the deflected orientation to the undeflected orientation when the external force is removed from the at least one of the patient reference array 100 and the impact absorber. Thus, the impact absorber is configured to, such as designed to, permit the patient reference array 100 to be returned to (e.g., realigned in) the undeflected orientation. Returning the patient reference array 100 to the undeflected position can reduce the likelihood that the computer-assisted surgery system will need to be re-calibrated. The impact absorber comprises at least one alignment feature that is configured to realign the reference array in the undeflected orientation when the reference array is moved from the deflected orientation to the undeflected orientation. The alignment feature can be configured to 1) engage with a corresponding alignment feature so as to align the reference array in the undeflected orientation and 2) disengage from the corresponding alignment feature when the reference array is rotated from the undeflected orientation to the deflected orientation.

In some embodiments, the impact absorber can be biased towards the undeflected orientation. Thus, the impact absorber can be configured to resiliently (e.g., automatically) rotate the reference array 100 relative to the medical implant 200 from the deflected orientation to the undeflected orientation when the external force is removed. Resilient rotating of the reference array 100 back to the undeflected orientation can be caused by the application of a counter-force on the at least one of the patient reference array 100 and the impact absorber. The counterforce can be caused by gravity, a spring force, an elastic force, any other suitable force, or any combination of suitable forces. In such embodiments, the system 10 can be considered to be a self-aligning system in that the system 10 automatically aligns the patient reference array 100 in the undeflected orientation when the external force is removed. In other embodiments, the impact absorber is configured to permit the reference array 100 to rotate relative to the medical implant 200 from the deflected orientation to the undeflected orientation when a manual external counter force is applied to at least one of the patient reference array 100 and the impact absorber. The manual external counter force can be applied by, for example, a healthcare professional or other party.

Figure 2:
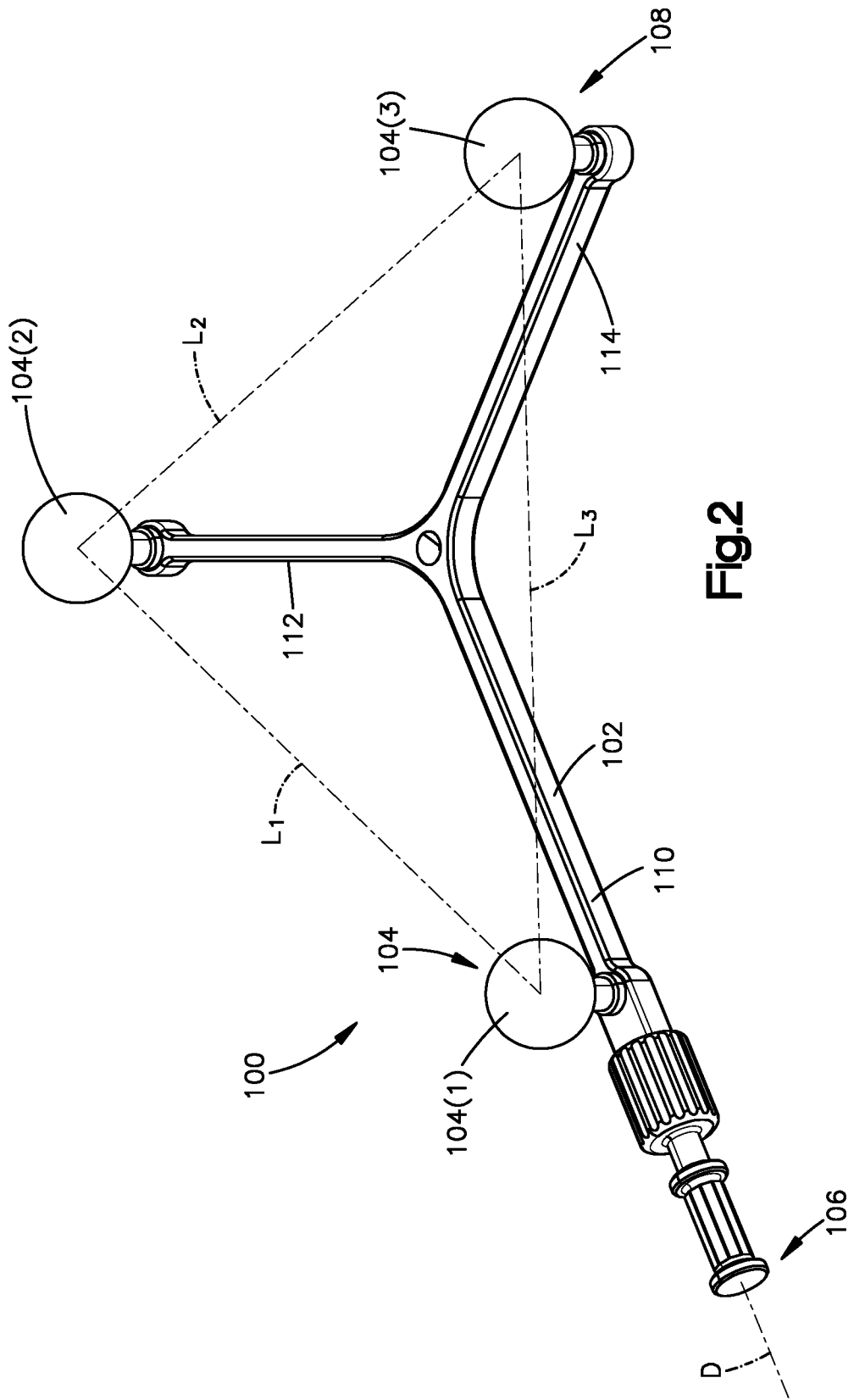
FIG. 2 shows a perspective view of the patient reference array of FIG. 1 according to one embodiment, the reference array having a body supporting a plurality of spherical markers.

With reference to FIG. 2, the patient reference array 100 can include a reference array body 102 and a plurality of markers 104 supported by the reference array body 102. The markers 104 can be positionally fixed relative to the reference array body 102 when the markers 104 are coupled to the reference array body 102, such that movement of the reference body 102 causes corresponding movement of the markers 104. The plurality of markers 104 define at least one reference point that is detectable by a computer of the computer-assisted surgery system so that movement of a surgical instrument can be navigated relative to the at least one reference point. The plurality of markers 104 can include at least two markers 104, such as at least three markers 104, or such as at least four markers 104. Each marker 104 can be a protrusion that can have any suitable shape. For example, each marker can have a spherical shape or a partially spherical shape. Each marker 104 can be a passive marker, such as a reflective marker, that can be detected by at least one sensor or camera of the computer-assisted surgery system without actively communicating with the computer of the computer-assisted surgery system. Alternatively, each marker can be an active marker, such as a light-emitting marker, that is configured to actively communicate with, or be detected by, the computing device of the computer-assisted surgery system.

The reference array body 102 can include a first end 106 and a second end 108 that are offset from one another. The first end 106 can be configured to removably couple to the impact absorber (e.g., 300, 400, 600, 700, 800). For example, the first end 106 can define a shaft that is configured to couple to the impact absorber (e.g., 300, 400, 600, 700, 800). In some embodiments, at least a portion of the first end 106 can have a non-circular cross-section that is configured to engage with a non-circular cross-section of an adapter 500 or the impact absorber so as to prevent rotation of the reference array 100 relative to the impact absorber. For example, the non-circular shape can be a hexagon, an octagon, or any other polygon or suitable shape. It will be understood, however, that the first end 106 can define other suitable shapes or can be fixedly attached to the impact absorber (e.g., 300, 400, 600, 700, 800), such as monolithic with, adhered to, welded to, or otherwise fixedly attached to the impact absorber (e.g., 300, 400, 600, 700, 800).

The reference array body 102 can support the plurality of markers 104 such that the plurality of markers 104 are aligned in a common plane. In one embodiment, as shown, the markers 104 can be supported so as to define a triangle that connects the geometric centers of the markers 104. For example, the reference array body 102 can have a Y-shape or T-shape. The Y- or T-shaped body 102 can have a first shaft 110 that extends from the first end 106 towards the second end 108 along a central axis D. The first shaft 110 can support a first marker 104(1) of the plurality of markers 104. The first marker 104(1) can be supported adjacent the first end 106. The reference array body 102 can have a second shaft 112 and a third shaft 114 that extend from opposed sides of the first shaft 110. The second and third shafts 112 and 114 can support second and third markers 104(2) and 104(3) of the plurality of markers 104, respectively. The second and third markers 104(2) and 104(3) can be supported at the second end 108. The first and second markers 104(1) and 104(2) can be aligned along a first line L1. The second and third markers 104(2) and 104(3) can be aligned along a second line L2. The first and third markers 104(1) and 104(3) can be aligned along a third line L3. At least one, up to all, of the first, second, and third lines can be angularly offset from one another. For example, the first and second lines L1 and L2 can define an angle therebetween that is less than or equal to 90 degrees. The second and third lines L2 and L3 can define an angle therebetween that is less than or equal to 90 degrees. The first and third lines L1 and L3 can define an angle therebetween that is less than or equal to 90 degrees. It will be understood that, in alternative embodiments, the reference array body 102 can have other suitable shapes and/or the markers 104 can be supported so as to define other suitable shapes.

Figure 9:
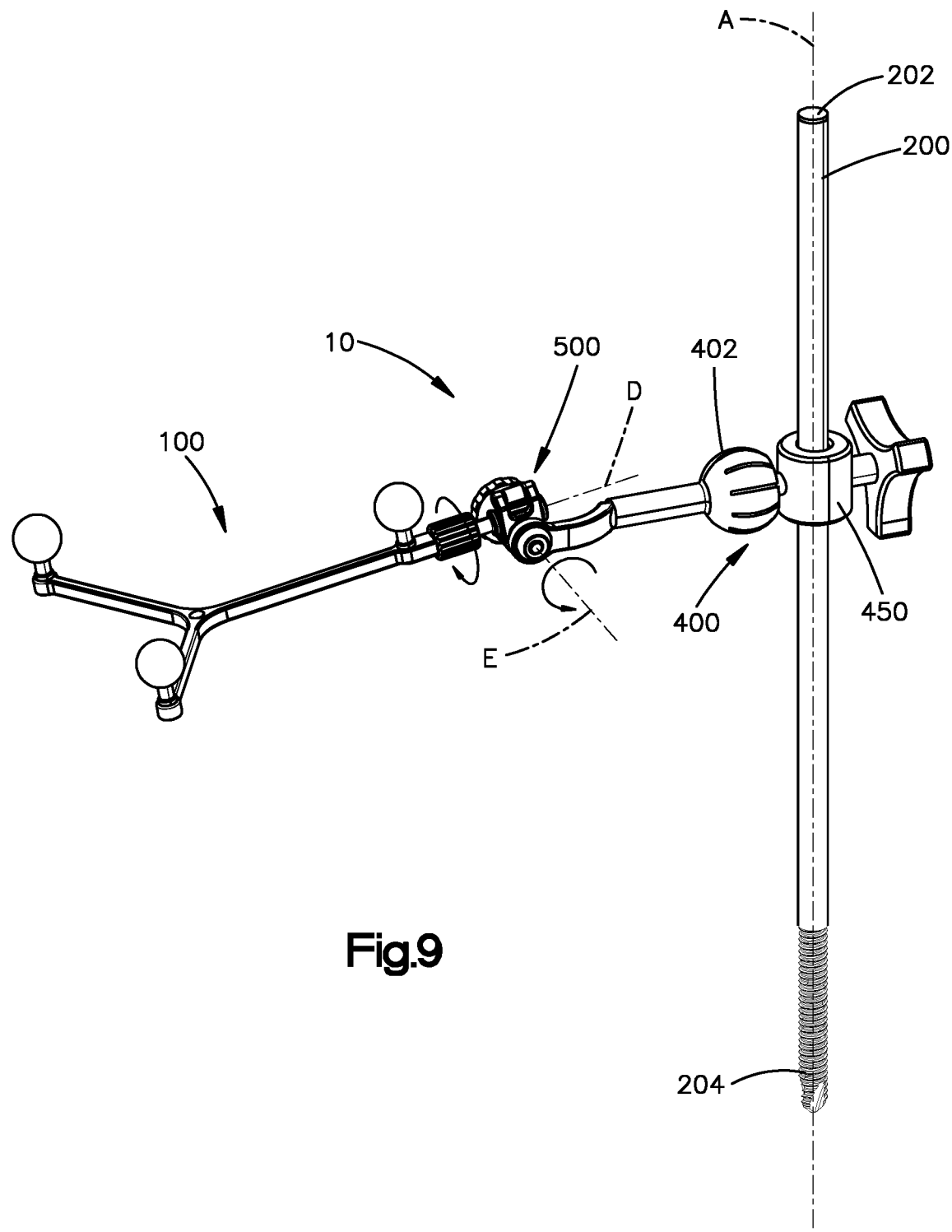
FIG. 9 shows a perspective view of a system having an impact absorber that couples a patient reference array to a medical implant according to another embodiment of the disclosure.

Returning now to FIGS. 1 and 9, the medical implant 200 can be a device that is configured to attach to a bone. For example, the medical implant 200 can be a bone anchor. The medical implant 200 can have a proximal end 202 and a distal end 204 that are offset from one another. At least a portion of the medical implant 200 can extend along an axial direction. For example, the medical implant 200 can extend from the proximal end 202 to the distal end 204 along a central axis A that extends along an axial direction. The medical implant 200 can define a shaft that extends between the proximal end 202 and distal end 204. The medical implant 200 can be elongate from the proximal end 202 to the distal end 204. The distal end 204 can be threaded such that the distal end 204 is configured to threadedly secure the medial implant 200 to a bone. In FIGS. 1 and 9, the bone anchor is illustrated as a Schanz screw. In alternative embodiments, the medical implant 200 can be a pin, a wire, a spinal rod, a pedicle screw, a pedicle hook, a lateral connector that connects first and second spinal rods to one another, or any other suitable medical implant. In embodiments where the medical implant 200 is a pedicle screw or hook, the reference array 100 can be configured to couple to a head or extension tabs of the pedicle screw or hook.

The impact absorber (e.g., 300, 400, 600, 700, 800) can be configured to support the patient reference array 100. For example, the impact absorber can be fixedly attached to the patient reference array 100, such as monolithic with, adhered to, welded to, or otherwise fixedly attached to the patient reference array 100. Alternatively, the impact absorber can be removably couplable to the patient reference array 100. For example, the system 10 can include an adapter 500 that is configured to removably couple the patient reference array 100 to the impact absorber. The adapter 500 can be implemented as a StarLink adapter manufactured by Brainlab AG, or as any other suitable adapter that can couple the patient reference array 100 to the impact absorber 100. In alternative embodiments, the system 10 can be implemented without the adapter 500.

The system 10 can include at least one joint that is configured to enable the reference array 100 to be selectively rotated about at least one axis so as to allow the patient reference array 100 to be repositioned relative to at least one sensor or camera of the computer-assisted surgery system. The at least one joint can be implemented by the adapter 500 or another suitable component of the system 10. The at least one joint can be configured to enable the reference array 10 to be selectively rotated about the central axis D of the patient reference array 100. Additionally, or alternatively, the at least one joint can be configured to enable the reference array 10 to be selectively rotated about an axis E that is perpendicular to the axis D of the reference array 100. The at least one joint can be configured to lock a position of the reference array 100 after the reference array 100 has been selectively rotated.

With specific reference to FIGS. 9 and 10, the adapter 500 can include a clamp 502. The clamp 500 can be configured to move between an unclamped position and a clamped position when the first end 106 of the reference array body 102 is received therein. In the unclamped position, the clamp 500 can permit the reference array 100 to (i) translate relative to the clamp 500 along a first direction that is parallel to the axis D of the patient array 100, and/or (ii) rotate relative to the clamp 500 about the axis D. In the clamped position, the clamp 500 positionally fixes the reference array 100 relative to the clamp 502 with respect to at least one, such as both, of (i) translation along the first direction that is parallel to the axis D of the patient reference array 100, and (ii) rotation about the axis D.

The clamp 502 can include a first plate 504 and a second plate 506. The first and second plates 504 and 506 can be offset from one another along the first direction. The first and second plates 504 and 506 can have inner surfaces 508 that face one another. In one embodiment, the inner surfaces 508 and can define at least one notch 510 that extends into at least one of the inner surfaces 508 and is configured to receive the first end 106 of the reference array body 102. For example, the inner surfaces 508 can define opposing notches 510. The at least one notch can have a non-circular cross-section that is configured to engage a non-circular cross-section of the first end 106 of the reference array body 102 so as to prevent the reference array 100 from rotating when the clamp 500 is in the clamped position. For example, the at least one notch can define a cross-sectional shape that is a hexagon, an octagon, or any other polygon or suitable shape.

The clamp 502 can include a hinge 512 that couples the first and second plates 504 and 506 to one another such that they are rotatable relative to one another. The hinge 512 can be define a pivot axis F that extends along the first direction that is parallel to the axis D. Thus, the first and second plates 504 and 506 can be configured to pivot about the pivot axis F towards one another to the clamped position and away from one another to the unclamped position.

The adapter 500 can include an actuator 501 configured to selectively control rotation of the reference array 100 relative to the impact absorber (e.g., 300, 400, 600, 700, 800) about an axis E that extends along a direction that is perpendicular to the axis D of the patient reference array 100. The actuator 501 can be configured to transition the adapter 500 between an unlocked configuration and locked configuration. In the unlocked configuration, the reference array 100 is permitted to rotate relative to the impact absorber (e.g., 300, 400, 600, 700, 800) about the axis E. In the locked configuration, the reference array 100 is rotationally fixed relative to the impact absorber (e.g., 300, 400, 600, 700, 800) with respect to rotation about the axis E.

To support the locked and unlocked configuration, the actuator 501, and hence the adapter 500, can include a fastener 520 that is configured to attach the clamp 502 to the impact absorber (e.g., 300, 400, 600, 700, 800). The fastener 520 can include a shaft 522 having a first end 524 and a second end 526. The first end 524 can be configured to attach to the impact absorber (e.g., 300, 400, 600, 700, 800). For example, the first end 524 can include threading that is configured to engage threading of the impact absorber (e.g., 300, 400, 600, 700, 800). The second end 526 can include a drive surface 528 that is configured to be engaged by a user or instrument to turn the fastener 520. In one example, the drive surface 528 can define a handle. The drive surface 528 can be enlarged to have a cross-sectional dimension that is greater than a cross-sectional dimension of the shaft 522.

The first and second plates 504 and 506 can each define an aperture 514 therethrough that is configured to receive the shaft 522 of the fastener 520. The apertures 514 can be aligned with one another so as to receive the shaft 522 therethrough. The fastener 520 extends through the clamp 502 such that the first end 524 extends out of the first plate 504 is a direction that extends from the second plate 506 to the first plate 504, and the second end 526 extends out of the second plate 506, opposite the first end 524, along a direction that extends from the first plate 504 to the second plate 506.

The adapter 500 can include a biasing element 540, such as a spring, that is disposed between the second end 526 of the fastener 520 (e.g., the handle), and the second plate 506. The biasing element 540 can be configured to bias the fastener 520 along a direction that extends from the first plate 504 towards the second plate 506. Thus, the biasing element 540 can be configured to urge the impact absorber (e.g., 300, 400, 600, 700, 800) against the outer surface of the first plate 504 when the fastener 520 is attached to the impact absorber (e.g., 300, 400, 600, 700, 800).

The force exerted by the biasing element 540 between the first plate 504 and the impact absorber (e.g., 300, 400, 600, 700, 800) can be sufficient to limit or prevent rotation of the reference array 100 relative to the impact absorber (e.g., 300, 400, 600, 700, 800), and hence relative to the medical implant 200. In some embodiments, the adapter 500 and the impact absorber (e.g., 300, 400, 600, 700, 800) can include mating geometries that mate with one another when the biasing element 540 biases the impact absorber (e.g., 300, 400, 600, 700, 800) against the adapter 500 so as to prevent rotation of the body 102 of the patient reference array 100 relative to the impact absorber (e.g., 300, 400, 600, 700, 800). For example, the first plate 504 can include a surface geometry 511 on an outer surface 509 of the first plate 504 that is configured to engage a corresponding surface geometry (see, for example, geometry 312 in FIGS. 7 and 12) of the impact absorber (e.g., 300, 400, 600, 700, 800). The surface geometry 511 can include a plurality of protrusions, such as teeth, that are spaced apart from one another by recesses. The protrusions and recesses of the surface geometry 511 can be configured to mate with corresponding protrusions and recesses of the impact absorber (e.g., 300, 400, 600, 700, 800) so as to fix a rotational position of the reference array 100. The protrusions and recesses can extend radially from the aperture 514 of the first plate 504. The protrusions and recesses can be offset from one another circumferentially around the aperture 514. It will be understood that the mating geometries can be configured in another manner.

In operation, an external force can be applied to the fastener 520 along an actuation direction that extends from the second plate 506 towards the first plate 504 so as to compress the biasing element 540. This in turn causes the first end 524 of the fastener 520, and hence the impact absorber (e.g., 300, 400, 600, 700, 800) attached to the first end 524, to move along the actuation direction such that the surface geometry of the impact absorber (e.g., 300, 400, 600, 700, 800) disengages from the surface geometry 511 of the adapter 500. While the external force is applied, the patient reference array 100 can be rotated relative to the impact absorber (e.g., 300, 400, 600, 700, 800) to a desired position. The external force can then be released so that the biasing element 540 urges the impact absorber (e.g., 300, 400, 600, 700, 800) against the adapter 500 so as to interlock the mating geometries of the impact absorber (e.g., 300, 400, 600, 700, 800) and the adapter 500, thereby fixing a position of the reference array 100 relative to the impact absorber (e.g., 300, 400, 600, 700, 800).

Turning now to the embodiment of FIGS. 1 and 5 to 8, the impact absorber 300 can have at least one body 302 defining a coupler that is configured to couple the reference array 100 to the medical implant 200. The at least one body 302, which can be referred to as a first body, movable body, or rotating body, can be configured to permit the reference array 100 to move relative to, such as rotate at least partially about, the medical implant 200 to a deflected orientation when an external force is applied to at least one of the reference array 100 and the impact absorber 300. For example, the first body 302 can be configured to permit the reference array 100 to rotate about the central axis A. In some embodiments, the impact absorber 300 can be configured to permit the reference array 100 to rotate in a manner that pivots relative to the medical implant 200 about a pivot point. Thus, in such embodiments, the reference array 100 can be pivotable relative to the medical implant 200. The first body 302 is configured to automatically rotate back to the undeflected orientation by gravity when the external force is removed. In alternative embodiments, the impact absorber 300 can include a spring that automatically rotates the first body 302 back to the undeflected orientaiton.

The impact absorber 300 can have a second body 350. The second body 350 can be configured to be positionally fixed relative to the medical implant 200 with respect to at least one, such as both, of translation along the central axis A and rotation about the central axis A. Thus, the second body 350 can be referred to as a fixed body. The first and second bodies 302 and 350 can be movably coupled to one another. For example, the first body 302 can be configured to rotate relative to the second body 350 about the central axis A.

The first body 302 can define a coupler 304, which can be referred to as a first coupler. The first coupler 304 can have an upper end 304a and a lower end 304b that are offset from one another along a central axis A. The lower end 304b can define a first guide surface 304c that is configured to guide rotational movement of the first body 302 about the central axis A. The first guide surface 304c can be configured to ride along a second guide surface, such as a guide surface 352c of the second body 350, as the first body 302 rotates relative to the medical implant 200. Alternatively, in embodiments that do not employ a second body 350, the guide surface 304c can be configured to ride along another suitable guide surface such as a guide surface (not shown) of the medical implant 200.

The first guide surface 304c can define a low point 304d. The guide surface 304c can be ramped upwards towards the upper end 304a as it extends away from the low point 304d. For example, the guide surface 304c can be ramped towards the upper end 304a as it extends away from the low point 304d in opposed rotational directions (e.g., clockwise and counterclockwise) about the central axis A. Stated differently, the guide surface 304c can be ramped downwards towards the lower end 304b as it extends towards the low point 304d in converging rotational directions (e.g., clockwise and counterclockwise) about the central axis A. The guide surface 304c can extend circumferentially around at least a portion, such as an entirety, of the lower end 304b about the central axis A.

The guide surface 304c can define a high point 304e at the lower end 304b. The guide surface 304c can be ramped upwards towards the upper end 304a as it extends towards the high point 304e. For example, the guide surface 304c can be ramped towards the upper end 304a as it extends towards the high point 304e in converging rotational directions (e.g., clockwise and counterclockwise) about the central axis A. Stated differently, the guide surface 304c can be ramped downwards towards the lower end 304a as it extends away from the high point 304e in opposing rotational directions (e.g., clockwise and counterclockwise) about the central axis A. In some embodiments, the high point 304e can be opposite the low point 304d along a radial direction that extends radially from the central axis A.

The first coupler 304 can have an outer surface 304f that extends between the upper and lower ends 304a and 304b. The outer surface 304f can have a cylindrical shape or can have any other suitable shape. The first coupler 304 can have an inner surface 304g that is opposite the outer surface 304f. The inner surface 304g can define a channel 304h that extends at least partially through the first coupler 304. For example, the channel 304h can extend from the upper end 304a to the lower end 304b. At least a portion of the channel 304h can be sized and configured to receive a shaft of the medical implant 200 therethrough. Thus, the first coupler 304 can be configured to removably attach to the medical implant 200.

The first body 302 can have an arm 306 that extends from the first coupler 304. When coupled to the medical implant 200, the arm 306 can extend along a direction that is angularly offset from the axis A of the medical implant 200. For example, the arm 306 can extend along a direction that is substantially perpendicular to the axis A, although other angles are envisioned. However, in alternative embodiments, the first body 302 can be devoid of the arm 306 and can be configured to attach to the patient reference array 100. The arm 306 can be configured to support the patient reference array 100. The arm 306 can be attached to the first coupler 304 such that the arm 306 does not move relative to the first coupler 304. Thus, the arm 306 can be positionally fixed relative to the first coupler 304 such that movement of the arm 306 causes a corresponding movement of the first coupler 304. In some embodiments, the first coupler 304 can be fixedly attached to the arm 306. For example, the first coupler 304 can be integral with, adhered to, welded to, or otherwise fixedly attached to the arm 306. In other embodiments, the first coupler 304 can be configured to removably attach to the arm 306. The arm 306 can be attached to the first coupler 304 at the low point 304d. Alternatively, the arm 306 can be attached to the first coupler 304 at another location.

Figure 3:
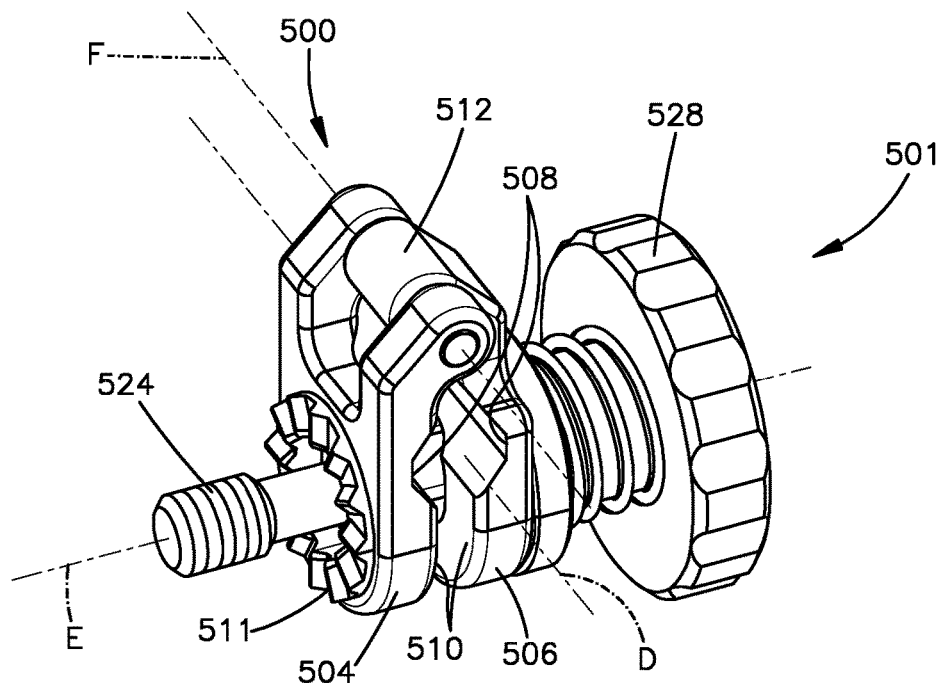
FIG. 3 shows a perspective view of an adapter of the patient reference array of FIG. 1 according to one embodiment, the adapter adapted to couple the reference array body of the patient reference array to the impact absorber.
Figure 4:
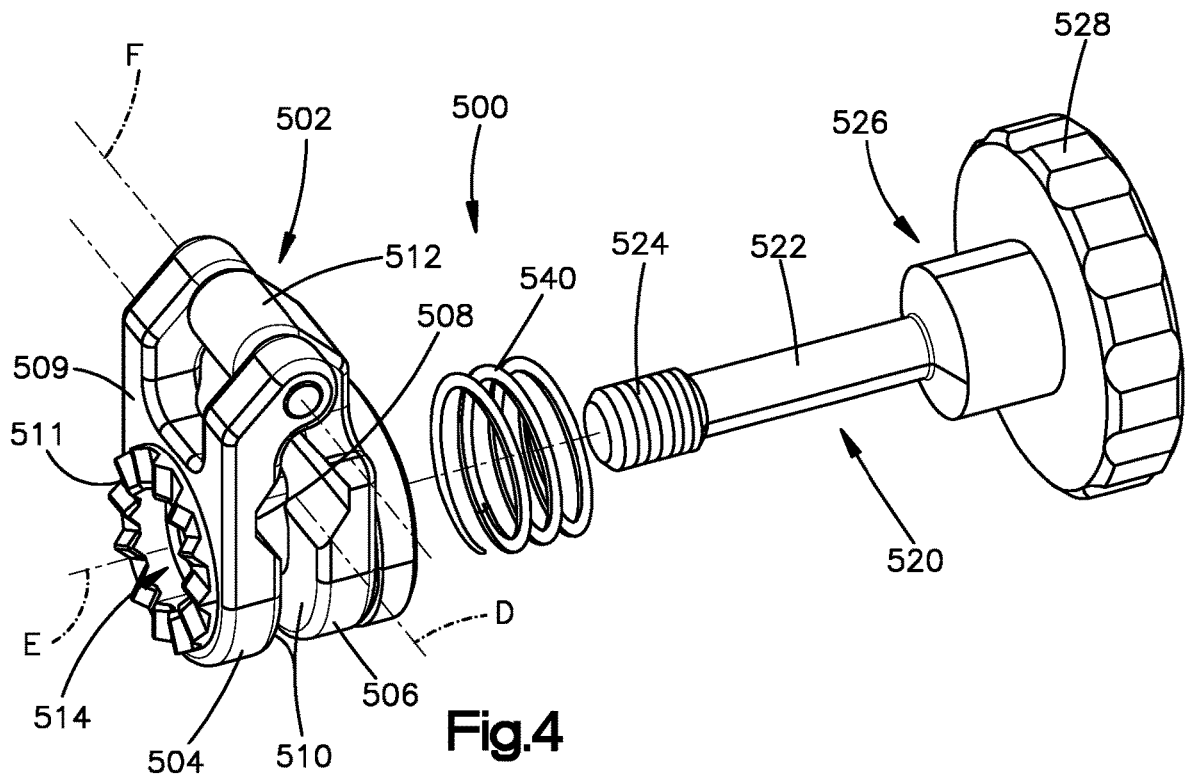
FIG. 4 shows an exploded perspective view of the adapter of FIG. 3 according to one embodiment.

The arm 306 can have a first end 306a and a second end 306b that are offset from one another. The arm 306 can define a shaft that extends between the first and second ends 306a and 306b. The second end 306b can be attached to the first coupler 304. The body 302 can define a coupler 308 that is configured to couple to the patient reference array 100. The coupler 308 can be defined at the first end 306a of the arm, although, in alternative embodiments in which the body 302 is devoid of the arm 306, the couple 308 can be attached to the first coupler 304. The coupler 308 can be referred to as a second coupler 308. In one example, the coupler 308 can define an opening 310 that is configured to receive the fastener 520 of the adapter 500 (see FIGS. 3 and 4). For example, the opening 310 can include internal threading that engages the threading of the first end 524 of the fastener 520 of the adapter 500. However, it will be understood that the first end 306a can be otherwise configured to couple to the patient reference array 100. In alternative embodiments, the arm 306 can be fixedly attached to the reference array 100, such as monolithic with, adhered to, welded to, or otherwise fixedly attached to the reference array 100.

The coupler 308 can include a surface geometry 312 on an outer surface of the arm 302 that is configured to engage a corresponding surface geometry 511 of the adapter 500. The surface geometry 312 can include a plurality of protrusions, such as teeth, that are spaced apart from one another by recesses. The protrusions and recess can extend radially from the opening 310. The protrusions and recesses can be offset from one another circumferentially around the opening 310. However, it will be understood that the surface geometry 511 can be configured in another manner. The protrusions and recesses of the surface geometry 312 can be configured to mate with corresponding protrusions and recesses of the adapter 500 so as to fix a rotational position of the reference array 100 relative to the impact absorber 300, and hence relative to the medical implant 200.

The second body 350 can define a coupler 352. The coupler 352 can have an upper end 352a and a lower end 352b that are offset from one another along a central axis A. The upper end 304a can define a guide surface 352c, which can be referred to as a second guide surface, that is configured to guide rotational movement of the first body 302 about the central axis A. The second guide surface 352c can define a valley 352d that extends into the upper end 352a along a direction that extends from the upper end 352a towards the lower end 352b. The second guide surface 352c can be ramped upwards towards the upper end 352a as it extends away from the valley 352d. For example, the second guide surface 352c can be ramped towards the upper end 352a as it extends away from the valley 352d in opposed rotational directions (e.g., clockwise and counterclockwise) about the central axis A. Stated differently, the second guide surface 352c can be ramped downwards towards the lower end 352b as it extends towards the valley 352d in converging rotational directions (e.g., clockwise and counterclockwise) about the central axis A. The second guide surface 352c can extend circumferentially around at least a portion, such as an entirety, of the upper end 352a about the central axis A.

The second guide surface 352c can define a peak 352e at the upper end 352a. The second guide surface 352c can be ramped upwards towards the upper end 352a as it extends from the valley 352d towards the peak 352e. For example, the second guide surface 352c can be ramped towards the upper end 352a as it extends towards the peak 352e in converging rotational directions (e.g., clockwise and counterclockwise) about the central axis A. Stated differently, the second guide surface 352c can be ramped downwards towards the lower end 352b as it extends away from the peak 352e in opposing rotational directions (e.g., clockwise and counterclockwise) about the central axis A. In some embodiments, the peak 352e can be opposite the valley 352d along a radial direction that extends radially from the central axis A.

The second body 350 can have an outer surface 352f that extends between the upper and lower ends 352a and 352b. The outer surface 352f can have a cylindrical shape or can have any other suitable shape. The second body 350 can have an inner surface 352g that is opposite the outer surface 352f. The inner surface 352g can define a channel 352h that extends at least partially through the coupler 352. For example, the channel 352h can extend from the upper end 352a to the lower end 352b. At least a portion of the channel 352h can be sized and configured to receive a shaft of the medical implant 200 therethrough. Thus, the second body 350 can be configured to removably attach to the medical implant 200. However, in alternative embodiments, the second body 350 can be fixedly attached to the medical implant 200. For example, the second body 350 can be integral with, adhered to, welded to, or otherwise fixedly attached to the medical implant 200.

The second body 350 can be configured such that, when the second body 350 is attached to the medical implant 200, the second body 350 does not move relative to the medical implant 200. Thus, the second body 350 can be configured to be positionally fixed relative to the medical implant 200 when the second body 350 is attached to the medical implant 200. For example, the second body 350 can be positionally fixed relative to the medical implant 200 with respect to translation along the central axis A and with respect to rotation about the central axis A.

The impact absorber 300 can be configured such that the reference array 100 can be reliably and repeatedly returned from the deflected orientation to the undeflected orientation. For example, the impact absorber 300 can be configured to click or snap into place when the reference array 100 is rotated to the undeflected orientation. The impact absorber 300 can be configured such that a first external force is needed move the reference array 100 from the undeflected orientation to a first deflected orientation, and a second external force is needed to further rotate the reference array 100 from the first deflected orientation to a second deflected orientation. The first external force can be greater than the second external force. Thus, the impact absorber 300, and in particular the at least one alignment feature, can resist movement of the reference array 100 from the undeflected orientation. However, the first and second external forces are less than an external force needed to cause the medical implant 200 to move relative to a bone to which the medical implant 200 is affixed.

In one example, the impact absorber 300 can define at least one alignment feature that is configured to engage a corresponding alignment feature of the system so as to align the impact absorber 300 in the undeflected orientation. The corresponding alignment feature can be part of another body of the impact absorber 300 or part of the medical implant 200. In some embodiments, the alignment feature can click or snap the impact absorber 300 in the undeflected orientation. As an example, the alignment feature can include one of a protrusion and a recess, and the corresponding alignment feature can include another of the protrusion and recess. For instance, the valley 352d of the coupler 352 can define a notch or recess that is configured to engage a corresponding protrusion 304j of the impact absorber 300 when the impact absorber 300 is in the undeflected orientation. The protrusion 304j can be defined by the second end of the arm 306 when the arm 306 is attached to the first coupler 304 at the low point 304d. Alternatively, the protrusion can extend downwardly from the guide surface 304c. The valley 352d can be shaped so as to conform to a shape of the protrusion 304j. Thus, the protrusion 304j can be configured to mate with the valley 352d. In some embodiments, the protrusion 304j and valley 352d can be keyed to one another. In alternative embodiments, the first body 302 can define the recess and the second body 350 can define the protrusion.

The first body 302 can be configured to move upwardly as the first body 302 is rotated relative to the second body 350 about the central axis A so as to move the protrusion 304j out of the valley 352d. The impact absorber 300 can be configured such that a first external force is needed move the to remove the protrusion 304j from the valley 352d (i.e., to move the reference array 100 from the undeflected orientation), and a second external force is needed to rotate the first and second bodies 302 and 350 relative to one another after the protrusion 304j is removed from the valley 352 (i.e., to move the reference array 100 from a first deflected orientation to a second deflected orientation). As described above, the first force can be greater than the second force.

The impact absorber 300 can include a fastener 370 that is configured to positionally fix the second body 350 to the medical implant 200. In one embodiment, the second coupler 352 can define a bore 352*j* that extends from the outer surface 352*f* to the inner surface 352*g*, and the fastener 370 can comprise a threaded fastener 370*a*, such as a screw. The threaded fastener 370*a* can be configured to threadedly engage the bore 352*j*, such that a distal end of the threaded fastener 370*a* extends through the bore 352*j* and applies a pressure to the medical implant 200 that fixes a position of the second body 350 relative to the medical implant 200. The fastener 370 can optionally comprise a drive surface 370*b* that is configured to be engaged by a hand or tool so as to turn the threaded fastener 370*a*. In one embodiment, the drive surface 370*b* can define a handle having a cross-sectional dimension that is greater than that of the threaded fastener 370*a*. It will be understood that, in alternative embodiments, the fastener 370 can configured as any other suitable fastener that can fix a position of the second body 350 relative to the medical implant 200.

In operation, when an external force is applied to the reference array 100 that is sufficient to deflect the reference array 100, the guide surface 304*c* of the first body 302 rides along the guide surface 352*c* of the second body 302, thereby causing (1) the alignment features 304*j* and 352*d* to disengage, and (2) the first body 302 to move along the central axis (e.g., upwardly) as it rotates about the central axis A along a first rotational direction. When the external force is removed, gravity causes the guide surface 304*c* of the first body 302 to ride along the guide surface 352*c* of the second body 350 along a second rotational direction, opposite the first rotational direction, until the alignment features 304*j* and 352*d* engage one another such that the reference array 100 is aligned in the undeflected orientation.

Turning now to the embodiment of FIGS. 9 to 13, an impact absorber 400 is shown that couples a patient reference array 100 to a medical implant 200. Note that reference array 100, the medical implant 200, the arm 306, and the adapter 500 can each be implemented as described above. The impact absorber 400 can have at least one body 402 that is configured to couple the reference array 100 to the medical implant 200. The at least one body 402, which can be referred to as a first body, movable body, or rotating body, can be configured to permit the reference array 100 to move relative to, such as rotate at least partially about, the medical implant 200 to a deflected orientation when an external force is applied to at least one of the reference array 100 and the impact absorber 400. For example, the first body 402, and hence the reference array 100, can be configured to rotate about at least one axis. Thus, the first body 402 can be referred to as a movable body or rotatable body. In some embodiments, the first body 402 can be configured to polyaxially rotate the reference array 100 such that the reference array 100 rotates about a plurality of axes. Further, in some embodiments, the impact absorber 400 can be configured to permit the reference array 100 to rotate in a manner that pivots relative to the medical implant 200 about a pivot point. Thus, in such embodiments, the reference array 100 can be pivotable relative to the medical implant 200. The first body 402 is configured to rotate back to the undeflected orientation when a manual external counter force is applied to at least one of the patient reference array 100 and the impact absorber 400.

The impact absorber 400 can have a second body 450. The second body 450 can be configured to be positionally fixed relative to the medical implant 200 with respect to at least one, such as both, of translation along the central axis A and rotation about the central axis A. Thus, the second body 450 can be referred to as a fixed body. The first and second bodies 402 and 450 can be movably coupled to one another. For example, the first body 402 can be configured to polyaxially rotate relative to the second body 450. The first body 402 can define one of a ball and a socket, and the second body 450 can define another one of the ball and the socket that is configured to mate with the one of the ball and the socket.

The first body 402 can have a coupler 404, which can be referred to as a first coupler. The first body 402 can have an arm 306 that extends from the first coupler 404. However, in alternative embodiments, the first body 402 can be devoid of the arm 306 and can be configured to attach to the patient reference array 100. The arm 306 can be configured as described above in relation to FIG. 7. The first coupler 404 can have a first end 404*a* and a second end 404*b* that are offset from one another along a central axis B. The coupler 404 can have an outer surface 404*c* that extends from the first end 404*a* to the second end 404*b*. The outer surface 404*c* can have a shape that is at least partially spherical, although the outer surface can have other suitable shapes. The coupler 404 can have an inner surface 404*d* opposite the outer surface 404*c*. The inner surface 404*b* can be curved. For example, the inner surface 404*b* can be curved along at least a first plane and a second plane that are perpendicular to one another.

The inner surface can define a recess 404*e*. The recess 404*e* can extend into the first end 404*a* towards the second end 404*b*. In at least some embodiments, the recess 404*e* can terminate before the second end 404*b* such that the second end 404*b* is closed. The recess 404*e* can have a shape that is at least partially spherical, such as at least hemispherical. The first coupler 404 can define a plurality of slots 404*f* that extend from the outer surface 404*c* to the inner surface 404*d* so as to define a plurality of flexible legs 404*g* therebetween. The flexible legs 404*g* can extend from the first end 44*a* towards the second end 404*b*. The flexible legs 404*g* can be configured to resiliently flex outwardly so as to receive a projection (e.g., 454) therein through the first end 404*a* and into the recess 404*e*, and then spring back inwardly so as to capture the projection in the recess 404*e*.

The second body 450 can have a coupler 452, which can be referred to as a first coupler. The coupler 452 can have an upper end 452*a* and a lower end 452*b* that are offset from one another along a central axis A. The second body 450 can have an outer surface 452*f* that extends between the upper and lower ends 452*a* and 452*b*. The outer surface 452*f* can have a cylindrical shape or can have any other suitable shape. The second body 450 can have an inner surface 452*g* that is opposite the outer surface 452*f*. The inner surface 452*g* can define a channel 452*h* that extends at least partially through the second coupler 452. For example, the channel 452*h* can extend from the upper end 452*a* to the lower end 452*b*. At least a portion of the channel 452*h* can be sized and configured to receive a shaft of the medical implant 200 therethrough. Thus, the second body 450 can be configured to removably attach to the medical implant 200. However, in alternative embodiments, the second body 450 can be fixedly attached to the medical implant 200. For example, the second body 450 can be integral with, adhered to, welded to, or otherwise fixedly attached to the medical implant 200.

The second body 450 can be configured such that, when the second body 450 is attached to the medical implant 200, the second body 450 does not move relative to the medical implant 200. Thus, the second body 450 can be configured to be positionally fixed relative to the medical implant 200 when the second body 450 is attached to the medical implant 200. For example, the second body 450 can be positionally fixed relative to the medical implant 200 with respect to translation along the central axis A and with respect to rotation about the central axis A.

The second body 450 can have a second coupler 454 that is configured to couple to the first body 402. The second coupler can include a projection 454 that extends from the coupler 452. The projection 454 can have a shape that is at least partially spherical, such as at least hemispherical. The projection 454 can be configured to be received in the recess 404e of the first coupler 405. Thus, the projection 454 and recess 404e can define a ball and socket joint. It will be understood that, in alternative embodiments, the first body 402 can define the projection 454 and the second body 450 can define the recess 404e. When the projection 454 is received in the recess 404e, the first body 402, and hence the reference array 100, can be configured to rotate (sch as pivot) polyaxially relative to the medical implant 200. For example, the first body 402, and hence the reference array 100, can be configured to pivot about a pivot point that is spaced from the central axis A of the medical implant 200. The pivot point can be defined by the projection 545. The first body 402, and hence the reference array 100, can be configured to pivot in a plurality of planes that extend through the pivot point.

The impact absorber 400 can be configured such that the reference array 100 can be reliably and repeatedly returned from the deflected orientation to the undeflected orientation. For example, the impact absorber 400 can be configured to click or snap into place when the reference array 100 is rotated to the undeflected orientation. The impact absorber 400 can be configured such that a first external force is needed move the reference array 100 from the undeflected orientation to a first deflected orientation, and a second external force is needed to further rotate the reference array 100 from the first deflected orientation to a second deflected orientation. The first external force can be greater than the second external force. Thus, the impact absorber 400, and in particular the alignment features, can resist movement of the reference array 100 from the undeflected orientation. However, the first and second external forces are less than an external force needed to cause the medical implant 200 to move relative to a bone to which the medical implant 200 is affixed.

In one example, the impact absorber 400 can define at least one alignment feature that is configured to engage a corresponding alignment feature of the system so as to align the impact absorber 400 in the undeflected orientation. The corresponding alignment feature can be part of another body of the impact absorber 400 or part of the medical implant 200. In some embodiments, the alignment feature can snap or click the impact absorber 400 in the undeflected orientation. As an example, the alignment feature can include one of a protrusion and a recess, and the corresponding alignment feature can include another of the protrusion and recess. For instance, the projection 454 can include one of a protrusion and a recess 456, and the inner surface 404d of the first coupler 404 can define another of the protrusion and recess 406 that is configured mate with the one of the protrusion and the recess 456. In some embodiments, the protrusion and recess can be keyed to one another, such that, when the protrusion and recess are mated with one another, the reference array 100 is in the undeflected orientation and in the proper rotational orientation.

The impact absorber 400 can include a fastener 370 that is configured to positionally fix the second body 350 to the medical implant 200. In one embodiment, the second coupler 352 can define a bore 452j that extends from the outer surface 452f to the inner surface 452g, and the fastener 370 can comprise a threaded fastener 370a, such as a screw. The threaded fastener 370a can be configured to threadedly engage the bore 452j, such that a distal end of the threaded fastener 370a extends through the bore 452j and applies a pressure to the medical implant 200 that fixes a position of the second body 450 relative to the medical implant 200. The fastener 370 can optionally comprise a drive surface 370b that is configured to be engaged by a hand or tool so as to turn the threaded fastener 370a. In one embodiment, the drive surface 370b can define a handle having a cross-sectional dimension that is greater than that of the threaded fastener 370a. It will be understood that, in alternative embodiments, the fastener 370 can configured as any other suitable fastener that can fix a position of the second body 450 relative to the medical implant 200.

In operation, when an external force is applied to the reference array 100 that is sufficient to deflect the reference array 100, the alignment features 406 and 456 disengage and the body 402 rotates relative to the medical implant 200 and the body 450 along at least one axis. When the external force is removed, a manual external force can be applied to at least one of the reference array 100 and the body 402 until the alignment features 406 and 456 engage one another such that the reference array 100 is aligned in the undeflected orientation.

Figure 16:
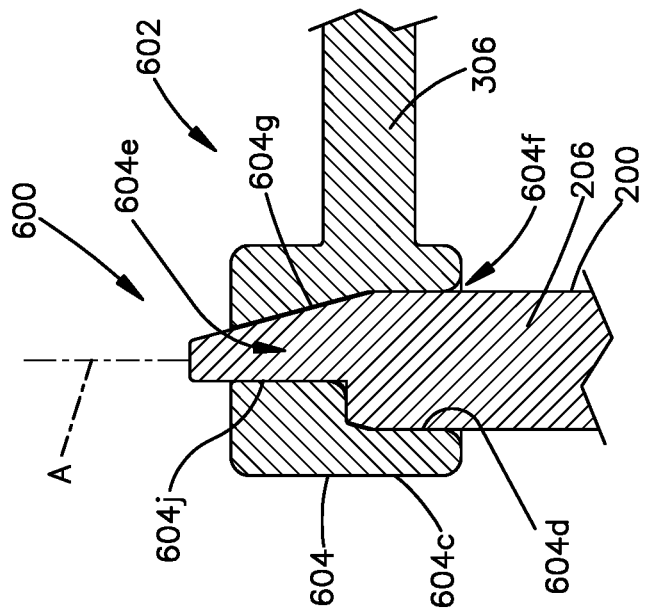
FIG. 16 shows a cross-sectional elevation view of the portion of the system of FIG. 14.
Figure 15:
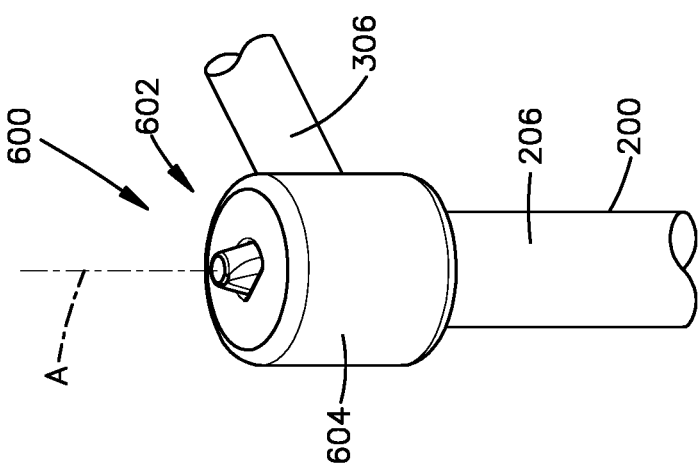
FIG. 15 shows an assembled perspective view of the portion of the system of FIG. 14.
Figure 14:
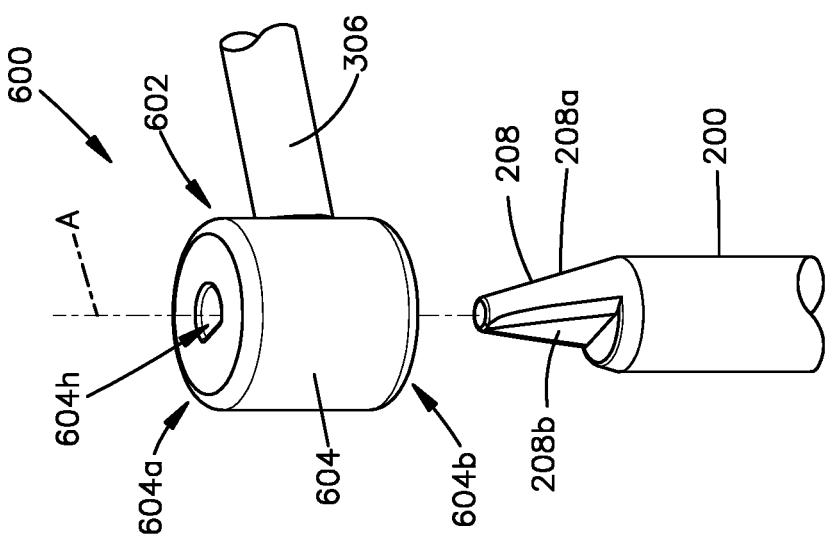
FIG. 14 shows an exploded perspective view of a portion of a system having an impact absorber that couples a patient reference array to a medical implant according to yet another embodiment of the disclosure.

Turning to FIGS. 14 to 16, an impact absorber 600 is shown that couples a patient reference array 100 to a medical implant 200. Note that reference array 100, the medical implant 200, and the adapter 500 are not shown but can each be implemented as described above. The impact absorber 600 can have a body 602 that is configured to couple the reference array 100 to the medical implant 200. The body 602 can be configured to permit the reference array 100 to move relative to, such as rotate at least partially about, the medical implant 200 to a deflected orientation when an external force is applied to at least one of the reference array 100 and the impact absorber 600. For example, the body 602, and hence the reference array 100, can be configured to rotate about at least one axis A. Thus, the body 602 can be referred to as a moving or rotating body. The axis A can be a central axis of a shaft of the implant 200. Further, in some embodiments, the impact absorber 600 can be configured to permit the reference array 100 to rotate in a manner that pivots relative to the medical implant 200 about a pivot point. Thus, in such embodiments, the reference array 100 can be pivotable relative to the medical implant 200. The body 602 is configured to automatically rotate back to the undeflected orientation by gravity when the external force is removed.

The body 602 can have a coupler 604 and an arm 306 that extends from the coupler 604. However, in alternative embodiments, the body 602 can be devoid of the arm 306 and can be configured to attach to the patient reference array 100. The arm 306 can be configured as described above in relation to FIG. 7. The coupler 604 can have a first end 604a and a second end 604b that are offset from one another along a central axis A. In some embodiments, the central axis A can be the central axis A of a shaft of the medical implant 200 when the body 602 is coupled to the medical implant 200.

The coupler 604 can have an outer surface 604c that extends from the first end 604a to the second end 604b. The outer surface 604c can have a shape that is at least partially cylindrical, although the outer surface can have other suitable shapes. The coupler 604 can have an inner surface 604d opposite the outer surface 604c. The inner surface 604d can define a channel 604h from the upper end 604a to the lower end 604b. The channel 604h can define a lower opening 604f at the lower end 604b that is sized to receive a shaft 206 of the medical implant 200. Thus, the second body 450 can be configured to removably attach to tip 208 of the medical implant 200. The channel 604h can define an upper opening 604e at the upper end 604a that can be sized to receive a tip 208 of the medical implant 200, without allowing the shaft 206 of the medical implant 200 to extend therethrough. Thus, the lower opening 604f can have a cross-sectional dimension that is greater than that of the upper opening 604e. It will be understood, however, that alternative embodiments can be implanted without the upper opening 604e.

The channel 604h can have a shape that conforms to a shape of the tip 208 of the medical implant 200. For example, the inner surface 604d can have a guide surface portion 604g that is configured to guide rotational movement of the body 602 about the central axis A. The guide surface portion 604g can be configured to ride along a guide surface portion 208a of the tip 208 of the medical implant 200. The guide surface portion 604g can have a shape, such as a partially-conical shape, that conforms to a shape, such as a partially-conical shape, of the guide surface portion 208a.

The inner surface 604d can also include an alignment feature 604j that is configured to engage a corresponding alignment feature 208b so as to align the impact absorber 600 into the undeflected orientation. The tip 208 of the medical implant 200 can define the corresponding alignment feature 208b. In some embodiments, the alignment feature can snap or click the impact absorber 600 into the undeflected orientation. As an example, the alignment feature 604j can include a non-circular cross-section that is configured to engage a non-circular cross-section of the implant 200. For instance, the alignment feature 604j of the impact absorber 600 and the corresponding alignment feature of the medical implant 200 can each include a surface that defines a plane, and the surfaces can be configured to engage one another so as to restrict rotation of the impact absorber 600 relative to the medical implant 200. The alignment feature 604j can include a portion of the inner surface 604d of the body 602 and the corresponding alignment feature 208b can include a surface of the medical implant 200. The portion of the inner surface 604d and the surface of the medical implant 200 can be substantially non-curved (e.g., flat or planar), although other shapes are contemplated. The non-curved portions of the inner surface 604d and tip 208 can engage one another so as to align the impact absorber 600 into the undeflected orientation, and so as to resist rotation from the undeflected orientation.

The impact absorber 600 can be configured such that a first external force is needed move the reference array 100 from the undeflected orientation to a first deflected orientation, and a second external force is needed to further rotate the reference array 100 from the first deflected orientation to a second deflected orientation. The first external force can be greater than the second external force. Thus, the impact absorber 600, and in particular the alignment features, can resist movement of the reference array 100 from the undeflected orientation. However, the first and second external forces are less than an external force needed to cause the medical implant 200 to move relative to a bone to which the medical implant 200 is affixed.

In operation, when an external force is applied to the reference array 100 that is sufficient to deflect the reference array 100, the guide surface 604g of the body 602 rides along the guide surface 208a of the medical implant 200, thereby causing (1) the alignment features 604j and 208b to disengage and (2) the body 602 to move along the central axis A (e.g., upwardly) as it rotates about the central axis A along a first rotational direction. When the external force is removed, gravity causes the guide surface 604g of the body 602 to ride along the guide surface 208a of the medical implant 200 along a second rotational direction, opposite the first rotational direction, until the alignment features 604j and 208b engage one another such that the reference array 100 is aligned in the undeflected orientation.

Turning now to FIGS. 17 to 19, an impact absorber 700 is shown that couples a patient reference array 100 to a medical implant 200. Note that reference array 100, the medical implant 200, and the adapter 500 are not shown but can each be implemented as described above. The impact absorber 700 can have a body 702 that is configured to couple the reference array 100 to the medical implant 200. The body 702 can be configured to permit the reference array 100 to move relative to, such as rotate at least partially about, the medical implant 200 to a deflected orientation when an external force is applied to at least one of the reference array 100 and the impact absorber 700. For example, the body 702, and hence the reference array 100, can be configured to rotate about at least one axis A. Thus, the body 702 can be referred to as a movable body or rotatable body. The axis A can be a central axis of a shaft of the implant 200. Further, in some embodiments, the impact absorber 700 can be configured to permit the reference array 100 to rotate in a manner that pivots relative to the medical implant 200 about a pivot point. Thus, in such embodiments, the reference array 100 can be pivotable relative to the medical implant 200. The body 702 is configured to rotate back to the undeflected orientation when a manual external counter force is applied to at least one of the patient reference array 100 and the impact absorber 700.

The body 702 can have a coupler 704 and an arm 306 that extends from the coupler 704. However, in alternative embodiments, the body 702 can be devoid of the arm 306 and can be configured to attach to the patient reference array 100. The arm 306 can be configured as described above in relation to FIG. 7. The coupler 704 can have a first end 704a and a second end 704b that are offset from one another along a direction that extends along the central axis A. In some embodiments, the central axis A can be the central axis A of a shaft of the medical implant 200 when the body 702 is coupled to the medical implant 200.

The coupler 704 can have an inner surface 704c, and an outer surface 704d opposite the inner surface 704c. The inner surface 704c can be configured to face the medical implant 200. For example, the inner surface 704c can be curved so as to conform to a shaft of the medical implant 200. Thus, the inner surface 704c can define a channel 706 that extends into an inner side of the coupler 704 towards an outer side of the coupler 704. The channel 706 can be open at the inner side, although embodiments of the disclosure are not so limited. The channel 706 can be configured to receive a shaft 206 of the medical implant 200.

The body 702 can have a fastener 708 that rotationally couples the impact absorber 700 to the medical implant 200. The fastener 708 can define a clip that extends from the coupler 704. The fastener 708 can have an inner surface 708a that is spaced opposite from, and faces, the inner surface 704c of the coupler 704 so as to define a space between the inner surface 708a of the fastener 708 and the inner surface 704c of the coupler 704. The fastener 708 can be resiliently biased towards the inner surface 704c such that, when the impact absorber 700 is coupled to the medical implant 200, the fastener 708 biases the medical implant 200 against the inner surface 704c.

The impact absorber 700 can be configured such that the reference array 100 can be reliably and repeatedly returned from the deflected orientation to the undeflected orientation. For example, the impact absorber 700 can be configured to click or snap into place when the reference array 100 is rotated to the undeflected orientation. The impact absorber 700 can be configured such that a first external force is needed move the reference array 100 from the undeflected orientation to a first deflected orientation, and a second external force is needed to further rotate the reference array 100 from the first deflected orientation to a second deflected orientation. The first external force can be greater than the second external force. Thus, the impact absorber 700, and in particular the alignment features, can resist movement of the reference array 100 from the undeflected orientation. However, the first and second external forces are less than an external force needed to cause the medical implant 200 to move relative to a bone to which the medical implant 200 is affixed.

In one example, the impact absorber 700 can define at least one alignment feature that is configured to engage a corresponding alignment feature so as to align the impact absorber 700 in the undeflected orientation. The corresponding alignment feature can be part of another body of the impact absorber 700 or part of the medical implant 200. In some embodiments, the alignment feature can click or snap the impact absorber 700 in the undeflected orientation. As an example, the alignment feature can include one of a protrusion and a recess, and the corresponding alignment feature can include another of the protrusion and recess. For instance, the inner surface 704c of the coupler 704 can include one of a recess and a protrusion 704e that is configured to engage another of a protrusion and a recess 206a of the medical implant 200 when the impact absorber 700 is in the undeflected orientation.

In operation, when an external force is applied to the reference array 100 that is sufficient to deflect the reference array 100, the alignment features 704e and 206a disengage. The external force can then cause the body 702 to deflect by at least one of (1) rotation relative to the medical implant 200 about the central axis A, and (2) translation along an axial direction (e.g., a direction that is perpendicular to the direction of rotation or that extends along the central axis A). When the external force is removed, a manual external force can be applied to at least one of the reference array 100 and the body 702 until the alignment features 704e and 206a engage one another such that the reference array 100 is aligned in the undeflected orientation.

Turning now to FIGS. 20 to 22, an impact absorber 800 is shown that couples a patient reference array 100 to a medical implant 200. Note that reference array 100, the medical implant 200, and the adapter 500 are not shown but can each be implemented as described above. The impact absorber 800 can have a body 802 that is configured to couple the reference array 100 to the medical implant 200. The body 802 can be configured to permit the reference array 100 to move relative to, such rotate as at least partially about, the medical implant 200 to a deflected orientation when an external force is applied to at least one of the reference array 100 and the impact absorber 800. For example, the body 802, and hence the reference array 100, can be configured to rotate about at least one axis A. Thus, the body 802 can be referred to as a movable body or rotatable body. The axis A can be a central axis of a shaft of the implant 200. Further, in some embodiments, the impact absorber 800 can be configured to permit the reference array 100 to rotate in a manner that pivots relative to the medical implant 200 about a pivot point. Thus, in such embodiments, the reference array 100 can be pivotable relative to the medical implant 200. The body 802 is configured to rotate back to the undeflected orientation when a manual external counter force is applied to at least one of the patient reference array 100 and the impact absorber 800.

The body 802 can have a coupler 804 and an arm 306 that extends from the coupler 804. However, in alternative embodiments, the body 802 can be devoid of the arm 306 and can be configured to attach to the patient reference array 100. The arm 306 can be configured as described above in relation to FIG. 7. The coupler 804 can have a first end 804a and a second end 804b that are offset from one another along a direction that extends along the central axis A. In some embodiments, the central axis A can be the central axis A of a shaft of the medical implant 200 when the body 802 is coupled to the medical implant 200.

The coupler 804 can have an inner surface 804c configured to face the medical implant 200. For example, the inner surface 804c can be curved so as to conform to a shaft of the medical implant 200. Thus, the inner surface 804c can define a recess 806 that extends into an inner side of the coupler 804 towards an outer side of the coupler 804. The recess 806 can be open at the inner side, although embodiments of the disclosure are not so limited. The recess 806 can be configured to receive a shaft 206 of the medical implant 200.

The body 802 can have a fastener 808 that rotationally couples the impact absorber 800 to the medical implant 200. The fastener 708 can have an inner surface 808a that is spaced opposite from, and faces, the inner surface 804c of the coupler 804 so as to define a space between the inner surface 808a of the fastener 808 and the inner surface 804c of the coupler 804. The fastener 808 can be resiliently biased towards the inner surface 804c such that, when the impact absorber 800 is coupled to the medical implant 200, the fastener 808 biases the medical implant 200 against the inner surface 804c. In one example, the fastener 808 can comprise a fastener body 808b and at least one spring 808c, such as a tension spring, that biases the fastener body 808b towards the inner surface 804c. The fastener body 808b can have a plate shape, although embodiments of the disclosure are not so limited. The at least one spring 808c can comprise a pair of springs 808c on opposed sides of the recess 806, where each spring 808c is coupled to both the coupler 804 and the fastener body 808b.

The impact absorber 800 can be configured such that the reference array 100 can be reliably and repeatedly returned from the deflected orientation to the undeflected orientation. For example, the impact absorber 700 can be configured to click or snap into place when the reference array 100 is rotated to the undeflected orientation. The impact absorber 800 can be configured such that a first external force is needed move the reference array 100 from the undeflected orientation to a first deflected orientation, and a second external force is needed to further rotate the reference array 100 from the first deflected orientation to a second deflected orientation. The first external force can be greater than the second external force. Thus, the impact absorber 800, and in particular the alignment features, can resist movement of the reference array 100 from the undeflected orientation. However, the first and second external forces are less than an external force needed to cause the medical implant 200 to move relative to a bone to which the medical implant 200 is affixed.

The impact absorber 800 can define at least one alignment feature that is configured to engage a corresponding alignment feature of the system so as to align the impact absorber 800 in the undeflected orientation. In some embodiments, the alignment feature can click or snap the impact absorber 800 in the undeflected orientation. In one example, the alignment feature can include one of a recess and a protrusion, and the corresponding alignment feature can include another of a recess and a protrusion. For instance, the inner surface 808a of the fastener body 808 can include one of a recess and a protrusion 808d that is configured to engage another of a protrusion and a recess 206a of the medical implant 200 when the impact absorber 800 is in the undeflected orientation.

Additionally, or alternatively, the alignment feature of the impact absorber 800 can include a non-circular cross-section that is configured to engage a non-circular cross-section of the implant 200. For example, the alignment feature of the impact absorber 800 and the corresponding alignment feature of the medical implant 200 can each include a surface that defines a plane, and the surfaces can be configured to engage one another so as to restrict rotation of the impact absorber 800 relative to the medical implant 200. The alignment feature can include the inner surface 808a of the fastener 808 and the corresponding alignment feature can include a surface 210 of the medical implant 200. The inner surface 808a and the surface 219 of the medical implant 200 can be substantially non-curved (e.g., flat or planar), although other shapes are contemplated.

In operation, when an external force is applied to the reference array 100 that is sufficient to deflect the reference array 100, the alignment features 808d and 206a disengage. The external force can then cause the body 802 to deflect by at least one of (1) rotation relative to the medical implant 200 about the central axis A, and (2) translation along an axial direction (e.g., a direction that is perpendicular to the direction of rotation or that extends along the central axis A). When the external force is removed, a manual external force can be applied to at least one of the reference array 100 and the body 802 until the alignment features 808d and 206a engage one another such that the reference array 100 is aligned in the undeflected orientation.

It should be noted that the illustrations and descriptions of the examples and embodiments shown in the figures are for exemplary purposes only, and should not be construed limiting the disclosure. One skilled in the art will appreciate that the present disclosure contemplates various embodiments. Additionally, it should be understood that the concepts described above with the above-described examples and embodiments may be employed alone or in combination with any of the other examples and embodiments described above. It should further be appreciated that the various alternative examples and embodiments described above with respect to one illustrated embodiment can apply to all examples and embodiments as described herein, unless otherwise indicated.

Unless explicitly stated otherwise, each numerical value and range should be interpreted as being approximate as if the word "about," "approximately," or "substantially" preceded the value or range. The terms "about," "approximately," and "substantially" can be understood as describing a range that is within 15 percent of a specified value unless otherwise stated.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Although there has been shown and described the preferred embodiment of the present disclosure, it will be readily apparent to those skilled in the art that modifications may be made thereto which do not exceed the scope of the appended claims. The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein. Accordingly, those skilled in the art will realize that the invention is intended to encompass all modifications and alternative arrangements included within the spirit and scope of the invention, as set forth by the appended claims.

What is claimed is:

1. An impact absorber, comprising:
   a body configured to support a reference array of a computer-assisted surgery system, the body comprising a coupler that is configured to couple to at least one of 1) a shaft of a medical implant and 2) a second body of the impact absorber that is configured to couple to the shaft, such that the reference array is rotatable with the body at least partially about the shaft from an undeflected orientation to a deflected orientation when an external force is applied to the reference array, and from the deflected orientation to the undeflected orientation when the external force is removed from the reference array so as to realign the reference array in the undeflected orientation.

2. The impact absorber of claim 1, wherein the body comprises an arm that extends from the coupler, the arm comprising a second coupler that is configured to couple to the reference array.

3. The impact absorber of claim 1, wherein the impact absorber is configured to resiliently rotate the reference array relative to the medical implant from the deflected orientation to the undeflected orientation when the external force is removed.

4. The impact absorber of claim 1, wherein the impact absorber is configured to resiliently rotate the reference array relative to the medical implant from the deflected orientation to the undeflected orientation by application of a counterforce that includes at least one of gravity, a spring force, or an elastic force.

5. The impact absorber of claim 1, wherein the impact absorber is configured to rotate the reference array relative to the medical implant from the deflected orientation to the undeflected orientation when a manual external counter force is applied to the patient reference array.

6. The impact absorber of claim 1, comprising an alignment feature that is configured to 1) disengage from a corresponding alignment feature when the reference array is rotated from the undeflected orientation to the deflected orientation and 2) engage with the corresponding alignment feature when the reference array is rotated from the deflected orientation to the undeflected orientation so as to realign the reference array in the undeflected orientation.

7. The impact absorber of claim 6, wherein the alignment feature includes one of a protrusion and recess, and the corresponding alignment feature includes another of the protrusion and recess.

8. The impact absorber of claim 6, wherein the alignment feature includes a non-circular cross-section that is configured to engage a non-circular cross-section of the corresponding alignment feature.

9. The impact absorber of claim 1, comprising the second body, wherein the second body defines a coupler configured to 1) couple to the medical implant so as to be positionally fixed relative to the medical implant and 2) rotatably couple to the body.

10. The impact absorber of claim 9, wherein the coupler of the body defines a guide surface that is configured to ride along a guide surface of the second body so as to guide rotational movement of the body relative to the second body.

11. The impact absorber of claim 9, wherein the second body comprises a second coupler that is configured to couple to the coupler of the body so as to define a ball and socket joint.

12. The impact absorber of claim 1, wherein the coupler of the body defines a channel that is configured to receive the shaft of the medical implant so as to couple to the shaft.

13. An impact absorber, comprising:
a body defining a coupler configured to couple a reference array of a computer-assisted surgery system to at least one of 1) a medical implant and 2) a second body of the impact absorber that is configured to couple to the medical implant, such that the reference array is movable with the body relative to the medical implant from an undeflected orientation to a deflected orientation when an external force is applied to the reference array and from the deflected orientation to the undeflected orientation when the external force is removed from the reference array; and
an alignment feature that is configured to 1) disengage from a corresponding alignment feature when the reference array is moved from the undeflected orientation to the deflected orientation and 2) engage with the corresponding alignment feature when the reference array is moved from the deflected orientation to the undeflected orientation so as to realign the reference array in the undeflected orientation.

14. The impact absorber of claim 13, wherein the alignment feature includes one of a protrusion and recess, and the corresponding alignment feature includes another of the protrusion and recess.

15. The impact absorber of claim 13, wherein the alignment feature includes a non-circular cross-section that is configured to engage a non-circular cross-section of the corresponding alignment feature.

16. The impact absorber of claim 13, wherein the coupler is configured to couple the reference array of the computer-assisted surgery system to the medical implant, and the corresponding alignment feature is defined by the medical implant.

17. The impact absorber of claim 13, comprising the second body, wherein the second body defines a coupler configured to couple to the medical implant so as to be positionally fixed relative to the medical implant, and the second body is configured to rotatably couple to the body.

18. The impact absorber of claim 17, wherein the corresponding alignment feature is defined by the second body.

19. The impact absorber of claim 13, wherein the impact absorber is configured to resiliently move the reference array relative to the medical implant from the deflected orientation to the undeflected orientation when the external force is removed.

20. The impact absorber of claim 13, wherein the impact absorber is configured to move the reference array relative to the medical implant from the deflected orientation to the undeflected orientation when a manual external counter force is applied to the patient reference array.

* * * * *